(12) United States Patent
Okada et al.

(10) Patent No.: US 9,181,205 B2
(45) Date of Patent: Nov. 10, 2015

(54) METHOD FOR PRODUCING OXAZOLE COMPOUND

(71) Applicant: OTSUKA PHARMACEUTICAL CO., LTD., Chiyoda-ku, Tokyo (JP)

(72) Inventors: Minoru Okada, Osaka (JP); Takashi Kabuki, Osaka (JP); Shigeo Fujieda, Osaka (JP); Nao Koseki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/423,896

(22) PCT Filed: Aug. 29, 2013

(86) PCT No.: PCT/JP2013/073854
§ 371 (c)(1),
(2) Date: Feb. 25, 2015

(87) PCT Pub. No.: WO2014/034958
PCT Pub. Date: Mar. 6, 2014

(65) Prior Publication Data
US 2015/0239855 A1  Aug. 27, 2015

Related U.S. Application Data

(60) Provisional application No. 61/695,056, filed on Aug. 30, 2012.

(51) Int. Cl.
*C07D 263/32* (2006.01)

(52) U.S. Cl.
CPC .................................. *C07D 263/32* (2013.01)

(58) Field of Classification Search
None
See application file for complete search history.

(56) References Cited

U.S. PATENT DOCUMENTS 6,472,386 B1    10/2002  Kodama et al.
8,637,559 B2 *   1/2014  Okada et al. .................. 514/374

FOREIGN PATENT DOCUMENTS

WO    WO 2007/058338 A3    5/2007

OTHER PUBLICATIONS

J.F. Sanz-Cervera et al., "Solution versus Fluorous versus Solid-Phase Synthesis of 2,5-Disubstituted 1,3-Azoles. Preliminary Antibacterial Activity Studies", J. Org. Chem., vol. 74, No. 23, pp. 8988-8996 (2009).
International Search Report from the European Patent Office for International Application No. PCT/JP2013/073854 mailed Nov. 15, 2013.
Written Opinion of the International Searching Authority from the European Patent Office for International Application No. PCT/JP2013/073854 mailed Nov. 15, 2013.

* cited by examiner

*Primary Examiner* — Kamal Saeed
(74) *Attorney, Agent, or Firm* — Finnegan, Henderson, Farabow, Garrett & Dunner, L.L.P.

(57) ABSTRACT

An object of the present invention is to provide a novel method for producing an oxazole compound. The invention relates to a method for producing a compound represented by formula (1): wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group or a group represented by formula: —$CY_2COOR^{12}$, wherein Y is a halogen atom, $R^{12}$ is an alkali metal atom or lower alkyl group, $Ar^1$ is phenyl group substituted with lower alkyl group, etc., or pyridyl group substituted with lower alkyl group, etc., $X^2$, $X^3$ and $X^9$ are the same or different and are halogen atoms, $X^4$ is a leaving group, and M is an alkali metal atom.

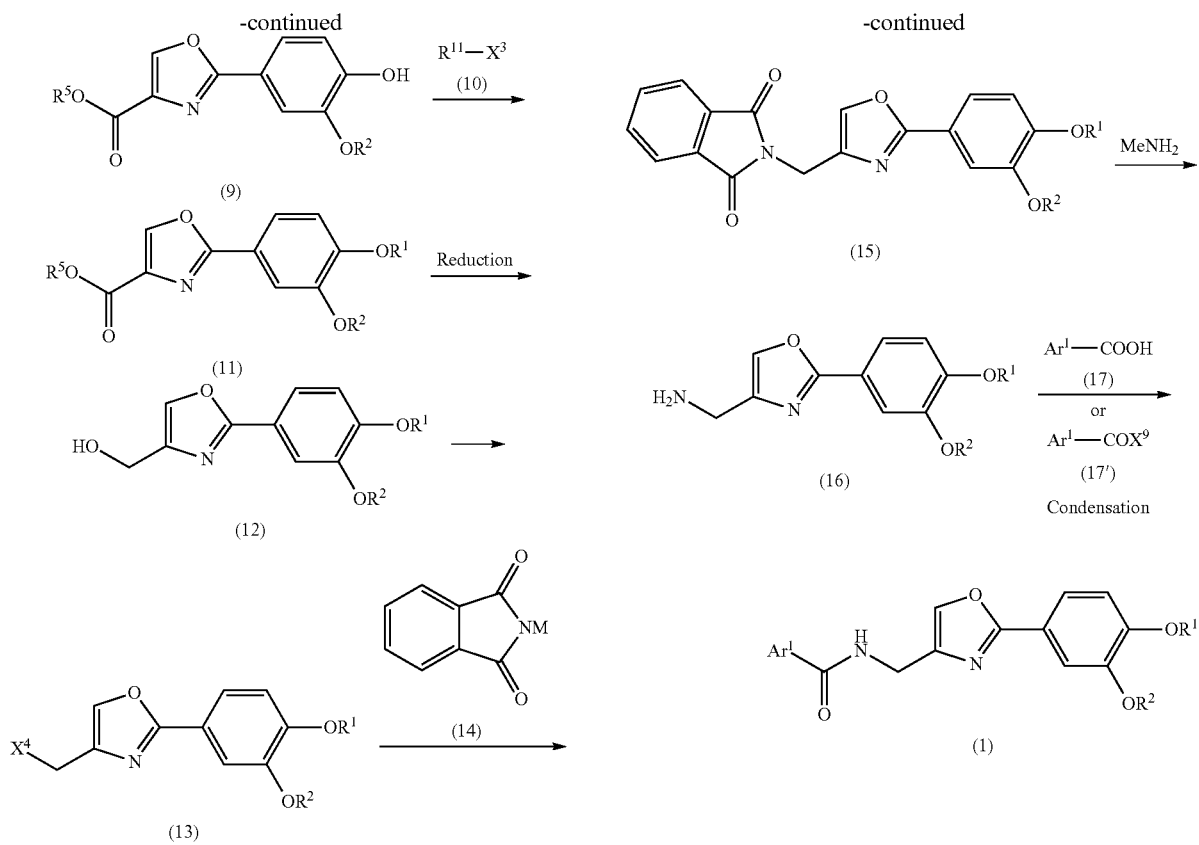
11 Claims, No Drawings

METHOD FOR PRODUCING OXAZOLE COMPOUND

TECHNICAL FIELD

The present invention relates to a novel method for producing an oxazole compound.

BACKGROUND ART

Patent Literature 1 reports an oxazole compound that exhibits a specific inhibitory activity against phosphodiesterase 4 (PDE4). Patent Literature 1 discloses a method for producing an oxazole compound. It indicates, as a typical method thereof, Reaction Scheme 1 to Reaction Scheme 12.

Among these, Reaction Scheme 10 discloses that compound (14) having an oxazole ring is produced by reacting dihaloketone compound (12) (specifically, 1,3-dichloro-2-propanone) with amide compound (13); and that primary amine compound (5a) is produced by reacting compound (16) having a phthalimide group with hydrazine (17).

However, because the starting material dihaloketone compound (12) exhibits strong stimulant and tearing properties; and, furthermore, because hydrazine (17) has a risk of explosion during the processes of concentration and dehydration, it is preferable to avoid the use thereof for the health and safety of the people involved in its production.

Furthermore, in the method for producing the oxazole compound disclosed in Patent Literature 1, purification by column chromatography is necessary in a plurality of processes, in addition to the processes in the above-mentioned Reaction Scheme 10.

However, in order to produce the target product on an industrial scale, a simple and effective production process in which expensive and complicated column chromatography is unnecessary throughout the process is required.

CITATION LIST

Patent Literature

PTL 1: WO No. 2007/058338 (JP2009-515872A)

SUMMARY OF INVENTION

Technical Problem

An object of the present invention is to provide a novel method for producing an oxazole compound.

Solution to Problem

The present inventors conducted extensive research to achieve the object of Patent Literature 1 described above, and found that the above-mentioned object can be achieved by employing the production method described below. Based on this finding, further research was conducted, and the present invention was thus accomplished.

The present invention provides the method for producing an oxazole compound described below.

Item 1. A compound represented by formula (12):

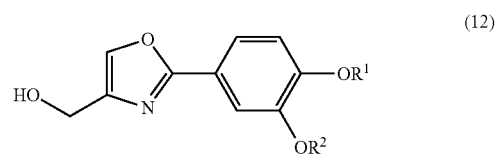

wherein $R^1$ is lower alkyl group or halogen substituted lower alkyl group, and $R^2$ is lower alkyl group.

Item 2. The compound according to Item 1, wherein in formula (12), $R^1$ is methyl or difluoromethyl group, and $R^2$ is methyl, isopropyl, or isobutyl group.

Item 3. A method for producing a compound represented by formula (12),

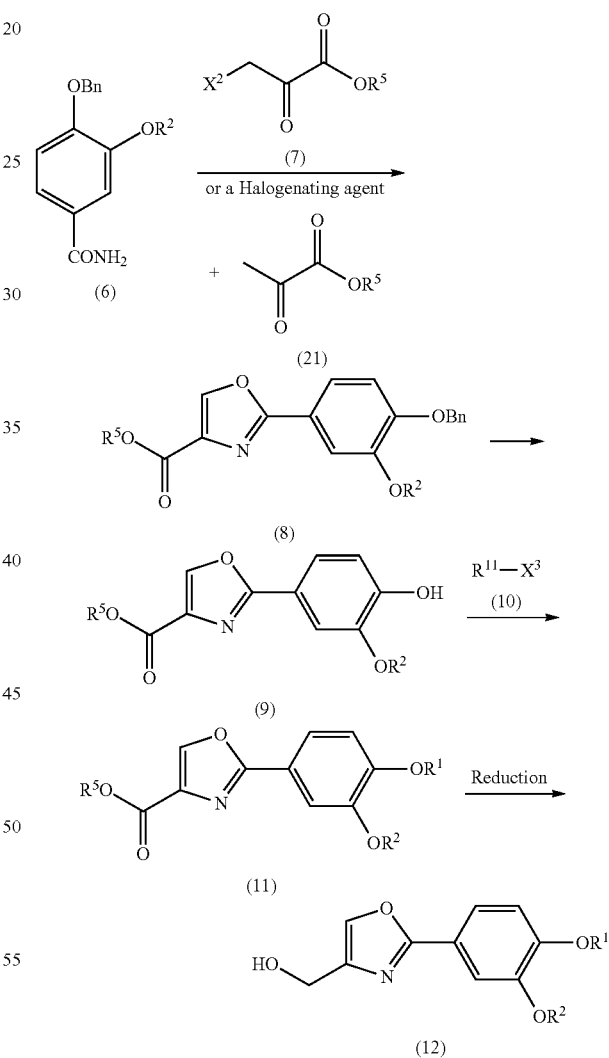

wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group, or a group represented by formula: $-CY_2COOR^{12}$, wherein Y is a halogen atom, $R^{12}$ is an alkali metal atom or lower alkyl group, and $X^2$ and $X^3$ are the same or different and are halogen atoms, the method comprising the steps of:

(a) reacting a compound represented by formula (6) with a compound represented by formula (7), or with a halogenating agent and a compound represented by formula (21) to obtain a compound represented by formula (8);

(b) debenzylating the compound represented by formula (8) to obtain a compound represented by formula (9);

(c) reacting the compound represented by formula (9) with a compound represented by formula (10) in the presence of a base to obtain a compound represented by formula (11); and (d) reducing the compound represented by formula (11) to obtain the compound represented by formula (12).

Item 4. The method for producing a compound represented by formula (12) according to Item 3,

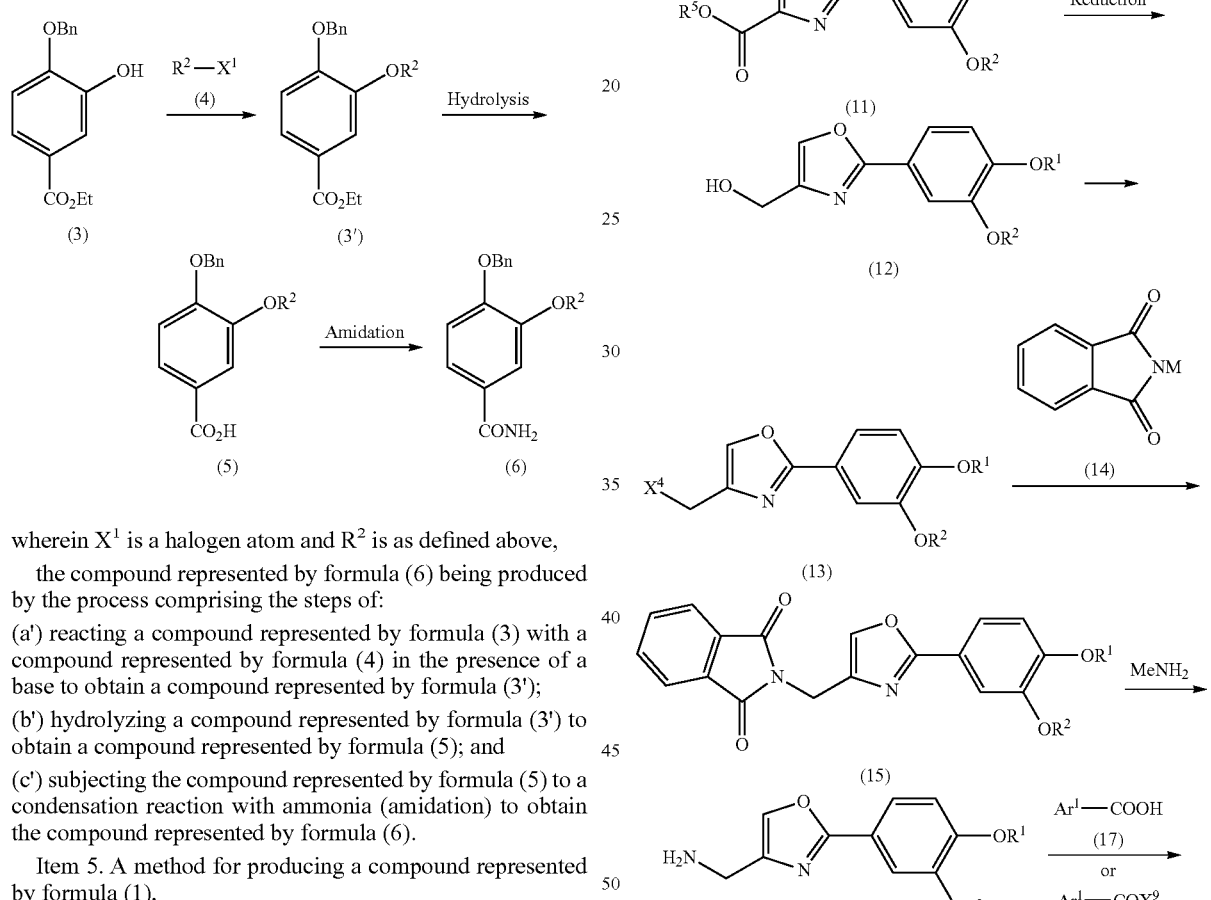

wherein $X^1$ is a halogen atom and $R^2$ is as defined above, the compound represented by formula (6) being produced by the process comprising the steps of:

(a') reacting a compound represented by formula (3) with a compound represented by formula (4) in the presence of a base to obtain a compound represented by formula (3');

(b') hydrolyzing a compound represented by formula (3') to obtain a compound represented by formula (5); and (c') subjecting the compound represented by formula (5) to a condensation reaction with ammonia (amidation) to obtain the compound represented by formula (6).

Item 5. A method for producing a compound represented by formula (1),

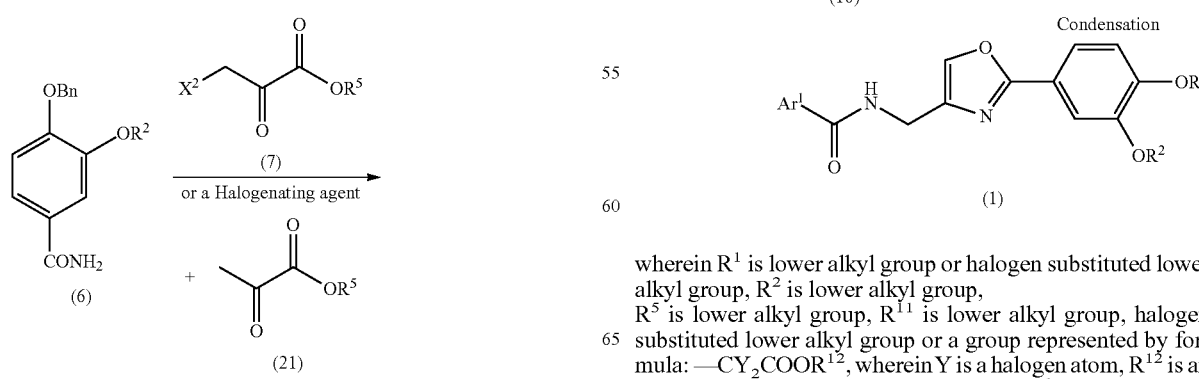

wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group or a group represented by formula: —$CY_2COOR^{12}$, wherein Y is a halogen atom, $R^{12}$ is an alkali metal atom or lower alkyl group, $Ar^1$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group, $X^2$, $X^3$ and $X^9$ are the same or different and are halogen atoms, $X^4$ is a leaving group, and M is an alkali metal atom, the method comprising the steps of:

(a) reacting a compound represented by formula (6) with a compound represented by formula (7), or with a halogenating agent and a compound represented by formula (21) to obtain a compound represented by formula (8);

(b) debenzylating the compound represented by formula (8) to obtain a compound represented by formula (9);

(c) reacting the compound represented by formula (9) with a compound represented by formula (10) in the presence of a base to obtain a compound represented by formula (11);

(d) reducing the compound represented by formula (11) to obtain a compound represented by formula (12);

(e) converting the hydroxyl group of the compound represented by formula (12) into a leaving group ($X^4$) to obtain a compound represented by formula (13);

(f) reacting the compound represented by formula (13) with a compound represented by formula (14) to obtain a compound represented by formula (15);

(g) reacting the compound represented by formula (15) with methylamine to obtain a compound represented by formula (16); and (h) subjecting the compound represented by formula (16) to a condensation reaction with a compound represented by formula (17) or with a compound represented by formula (17') to obtain the compound represented by formula (1).

Item 6. A method for producing a compound represented by formula (1),

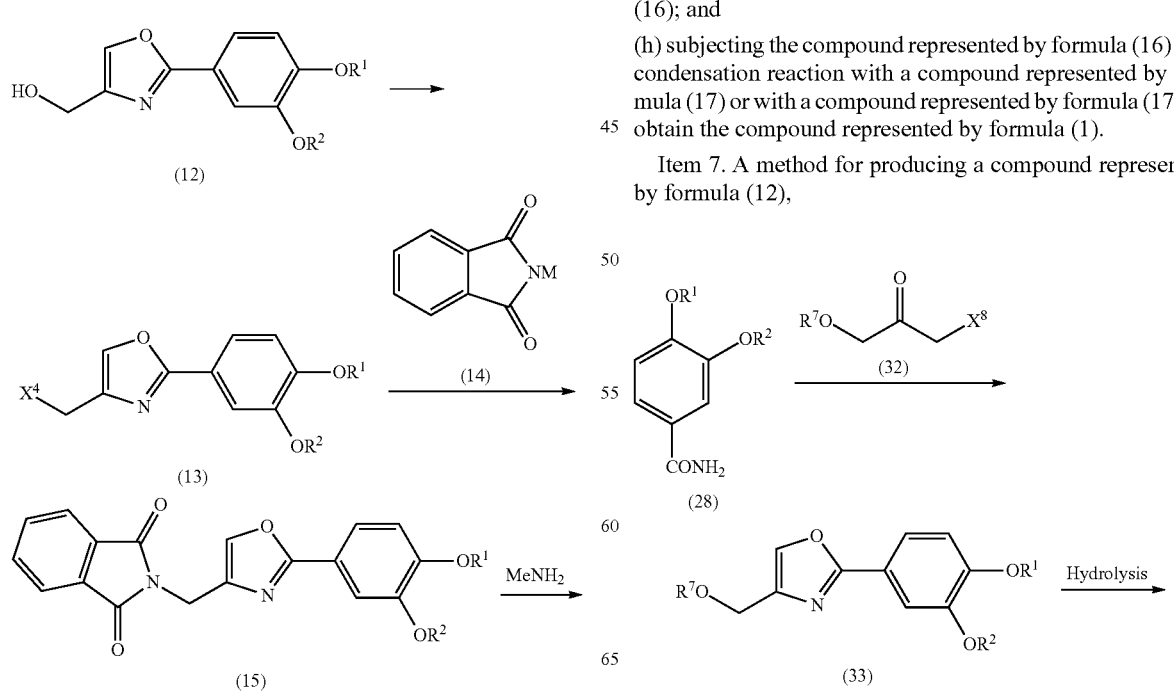

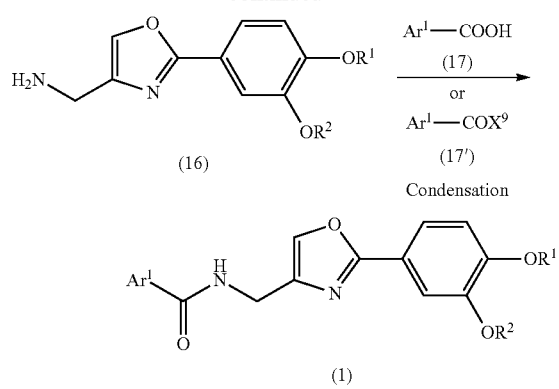

wherein $R^1$ is lower alkyl group or halogen substituted lower alkyl group, $R^2$ is lower alkyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^9$ is a halogen atom, $X^4$ is a leaving group, and M is an alkali metal atom, the method comprising the steps of:

(e) converting a hydroxyl group of the compound represented by formula (12) into a leaving group ($X^4$) to obtain a compound represented by formula (13);

(f) reacting the compound represented by formula (13) with a compound represented by formula (14) to obtain a compound represented by formula (15);

(g) reacting the compound represented by formula (15) with methylamine to obtain a compound represented by formula (16); and (h) subjecting the compound represented by formula (16) to a condensation reaction with a compound represented by formula (17) or with a compound represented by formula (17') to obtain the compound represented by formula (1).

Item 7. A method for producing a compound represented by formula (12),

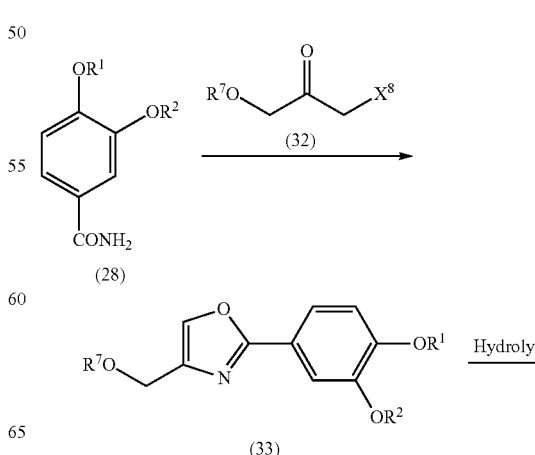

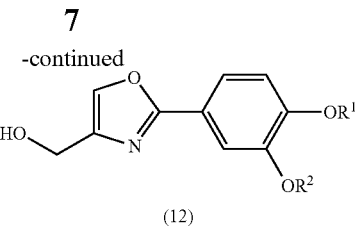

(12)

wherein $R^1$ is lower alkyl group or halogen substituted lower alkyl group, $R^2$ is lower alkyl group, $R^7$ is lower alkanoyl group, and $X^8$ is a halogen atom, the method comprising the steps of:
(a) reacting a compound represented by formula (28) with a compound represented by formula (32) to obtain a compound represented by formula (33); and
(b) hydrolyzing the compound represented by formula (33) to obtain the compound represented by formula (12).

Item 8. The method for producing a compound represented by formula (12) according to Item 7,

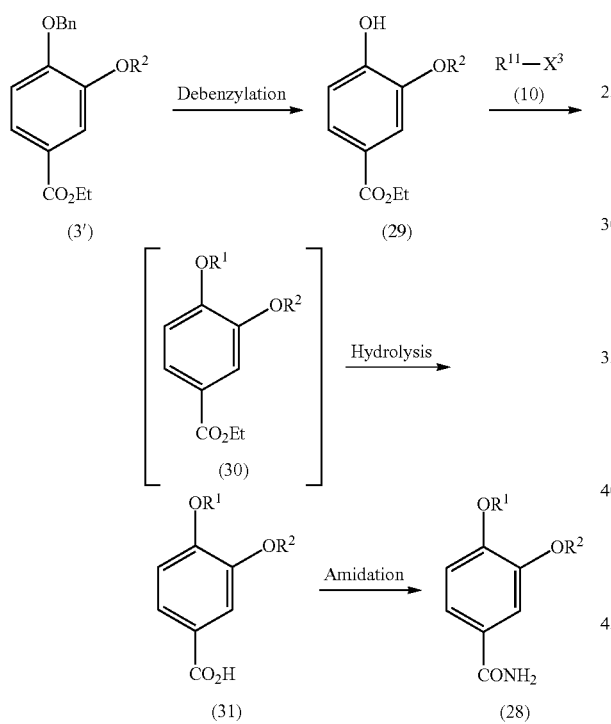

wherein $R^{11}$ is lower alkyl group, halogen substituted lower alkyl group or a group represented by formula: —$CY_2COOR^{12}$, wherein Y is a halogen atom, $R^{12}$ is an alkali metal atom or lower alkyl group, $X^3$ is a halogen atom, and $R^1$ and $R^2$ are as defined above, the compound represented by formula (28) being produced by the process comprising the steps of:
(a') debenzylating a compound represented by formula (3') to obtain a compound represented by formula (29);
(b') reacting the compound represented by formula (29) with a compound represented by formula (10) in the presence of a base to obtain a compound represented by formula (30);
(c') hydrolyzing the compound represented by formula (30) to obtain a compound represented by formula (31); and
(d') subjecting the compound represented by formula (31) to a condensation reaction with ammonia (amidation) to obtain the compound represented by formula (28).

Item 9. A method for producing a compound represented by formula (1),

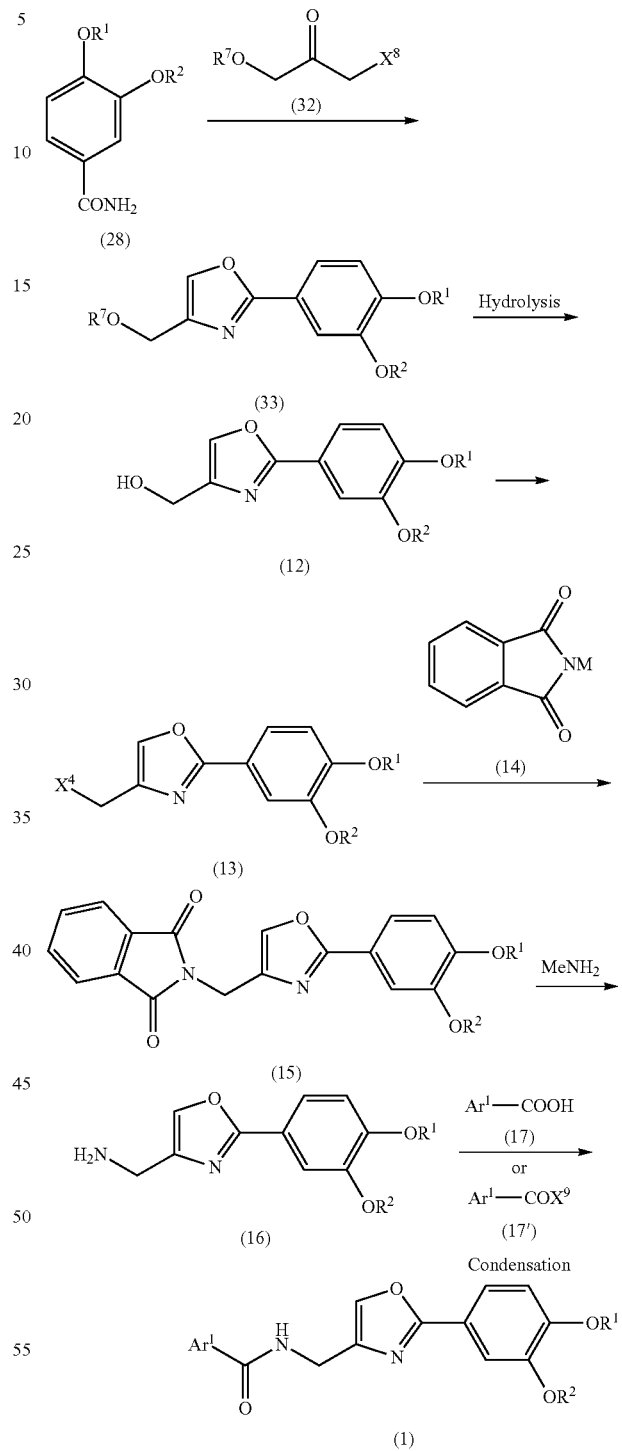

wherein $R^1$ is lower alkyl group or halogen substituted lower alkyl group, $R^2$ is lower alkyl group, $R^7$ is lower alkanoyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^4$ is a leaving group, $X^8$ and $X^9$ are the same or different and are halogen atoms, and M is an alkali metal atom, the method comprising the steps of:

(a) reacting a compound represented by formula (28) with a compound represented by formula (32) to obtain a compound represented by formula (33);

(b) hydrolyzing the compound represented by formula (33) to obtain a compound represented by formula (12);

(c) converting the hydroxyl group of the compound represented by formula (12) into a leaving group ($X^4$) to obtain a compound represented by formula (13);

(d) reacting the compound represented by formula (13) with a compound represented by formula (14) to obtain a compound represented by formula (15);

(e) reacting the compound represented by formula (15) with methylamine to obtain a compound represented by formula (16); and (f) subjecting the compound represented by formula (16) to a condensation reaction with a compound represented by formula (17) or with a compound represented by formula (17') to obtain the compound represented by formula (1).

Item 10. A method for producing a compound represented by formula (1),

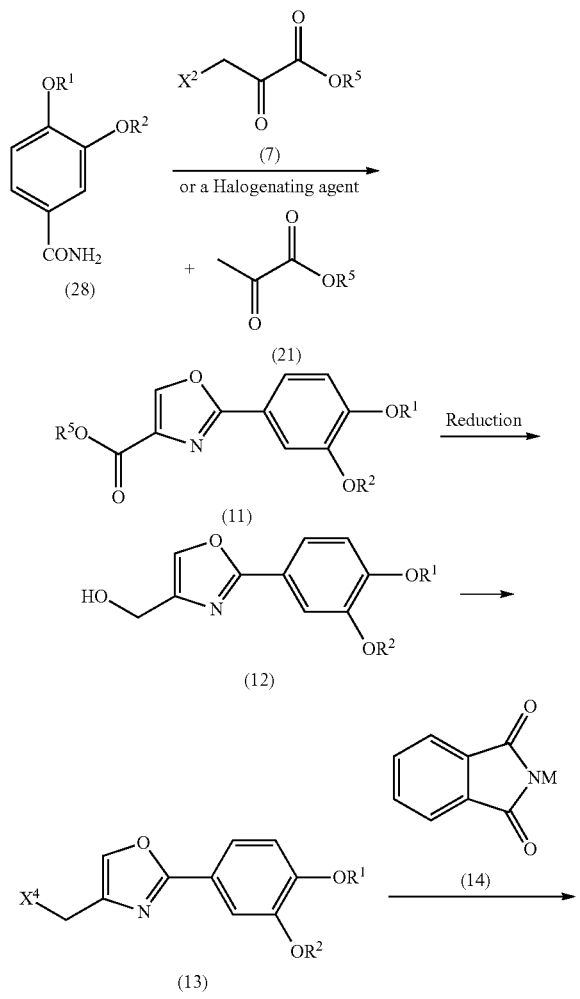

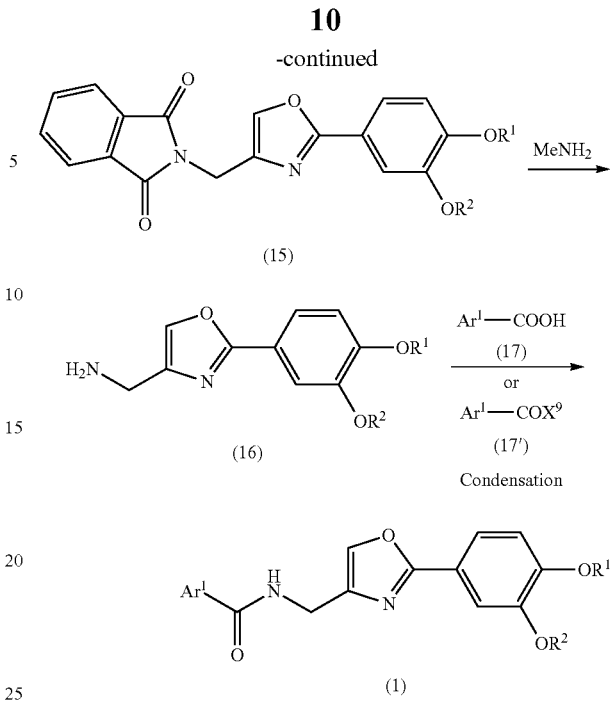

wherein $R^1$ is lower alkyl group or halogen substituted lower alkyl group, $R^2$ is lower alkyl group, $R^5$ is lower alkyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^2$ and $X^9$ are the same or different and are halogen atoms, $X^4$ is a leaving group, and M is an alkali metal atom, the method comprising the steps of:

(a) reacting a compound represented by formula (28) with a compound represented by formula (7) or with a halogenating agent and the compound represented by formula (21) to obtain a compound represented by formula (11);

(b) reducing the compound represented by formula (11) to obtain a compound represented by formula (12);

(c) converting the hydroxyl group of the compound represented by formula (12) into a leaving group ($X^4$) to obtain a compound represented by formula (13);

(d) reacting the compound represented by formula (13) with a compound represented by formula (14) to obtain a compound represented by formula (15);

(e) reacting the compound represented by formula (15) with methylamine to obtain a compound represented by formula (16); and (f) subjecting the compound represented by formula (16) to a condensation reaction with a compound represented by formula (17) or with a compound represented by formula (17') to obtain the compound represented by formula (1).

Item 11. A method for producing a compound represented by formula (2),

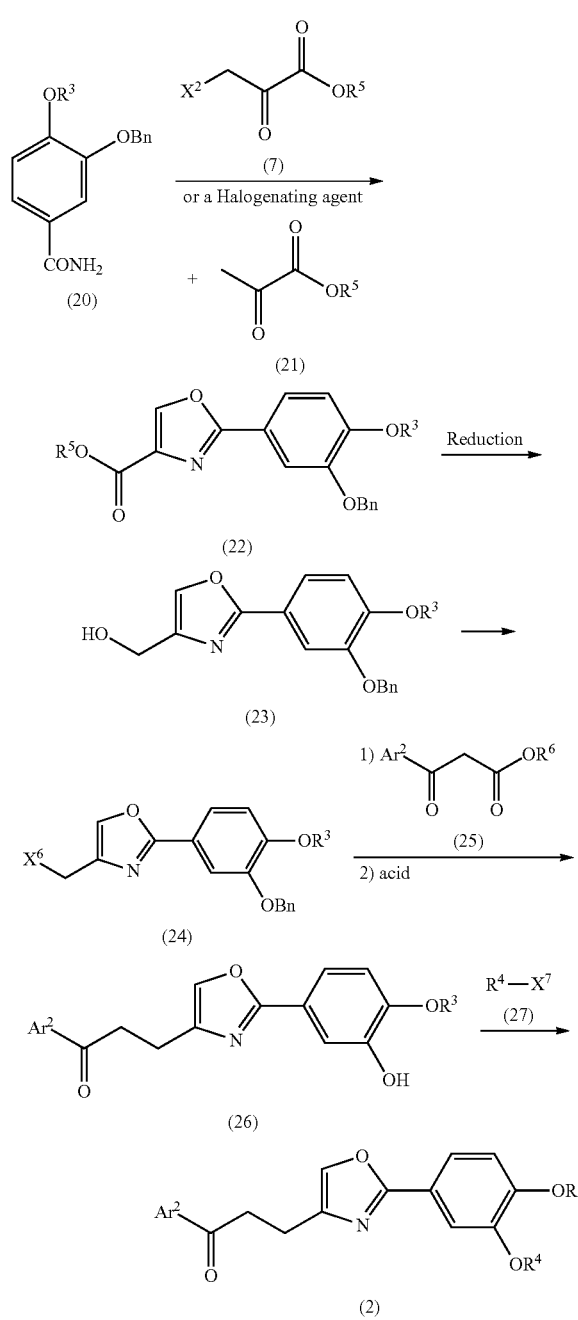

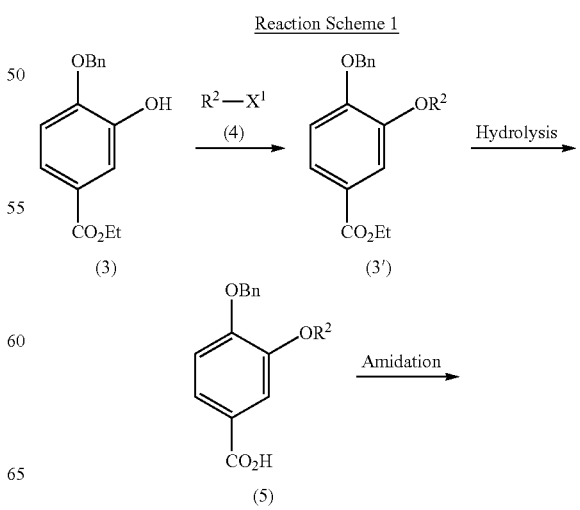

the method comprising the steps of:

(a) reacting a compound represented by formula (20) with a compound represented by formula (7), or with a halogenating agent and a compound represented by formula (21) to obtain a compound represented by formula (22);

(b) reducing the compound represented by formula (22) to obtain a compound represented by formula (23);

(c) converting the hydroxyl group of the compound represented by formula (23) into a leaving group ($X^6$) to obtain a compound represented by formula (24);

(d) reacting the compound represented by formula (24) with a compound represented by formula (25) and then treating the resultant with an acid to obtain a compound represented by formula (26); and (e) reacting the compound represented by formula (26) with a compound represented by formula (27) in the presence of a base to obtain the compound represented by formula (2).

Advantageous Effects of Invention

The present invention relates to a novel method for producing an oxazole compound. Because this method does not use a dihaloketone compound and hydrazine throughout the production processes thereof, it is preferable from the viewpoint of the health and/or safety of the people who are involved in its production. Furthermore, because this method allows the isolation and purification of the target product without using expensive and complicated column chromatography throughout the production process, it is preferably employed as an effective method on an industrial scale.

DESCRIPTION OF EMBODIMENTS

The present invention is explained in detail below.

1. Method for Producing Compound Represented by Formula (1)

The compound represented by formula (1) can be produced through the reaction steps shown in Reaction Scheme 1.

wherein $R^3$ is lower alkyl group or halogen substituted lower alkyl group, $R^4$ is lower alkyl group, cycloalkyl-lower alkyl group, or lower alkenyl group, $R^5$ is lower alkyl group, $R^6$ is lower alkyl group, $Ar^2$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group, $X^2$ and $X^7$ are the same or different and are halogen atoms, and $X^6$ is a leaving group,

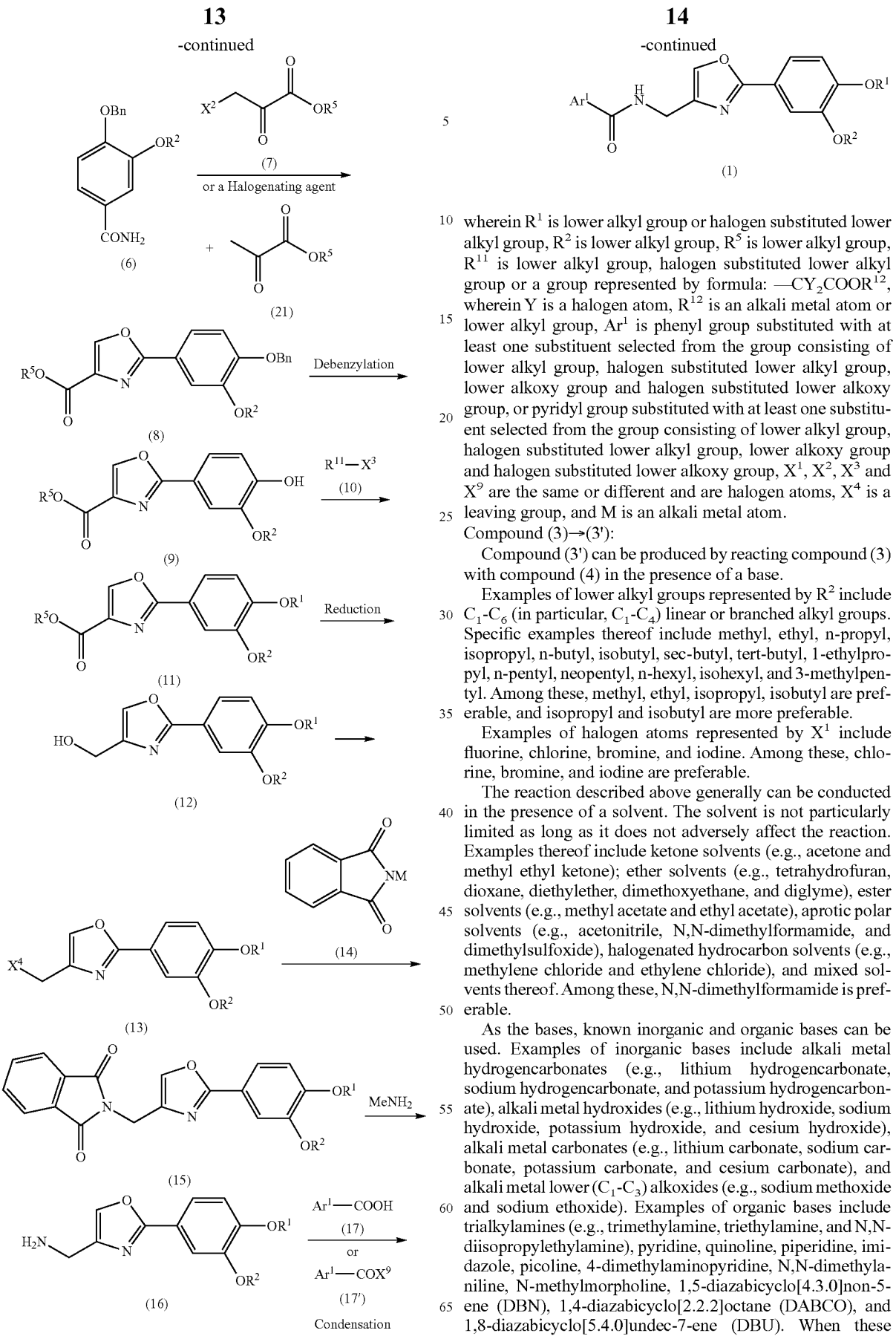

wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group or a group represented by formula: $-CY_2COOR^{12}$, wherein Y is a halogen atom, $R^{12}$ is an alkali metal atom or lower alkyl group, $Ar^1$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group, $X^1$, $X^2$, $X^3$ and $X^9$ are the same or different and are halogen atoms, $X^4$ is a leaving group, and M is an alkali metal atom.

Compound (3)→(3'):

Compound (3') can be produced by reacting compound (3) with compound (4) in the presence of a base.

Examples of lower alkyl groups represented by $R^2$ include $C_1$-$C_6$ (in particular, $C_1$-$C_4$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl, ethyl, isopropyl, isobutyl are preferable, and isopropyl and isobutyl are more preferable.

Examples of halogen atoms represented by $X^1$ include fluorine, chlorine, bromine, and iodine. Among these, chlorine, bromine, and iodine are preferable.

The reaction described above generally can be conducted in the presence of a solvent. The solvent is not particularly limited as long as it does not adversely affect the reaction. Examples thereof include ketone solvents (e.g., acetone and methyl ethyl ketone); ether solvents (e.g., tetrahydrofuran, dioxane, diethylether, dimethoxyethane, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, N,N-dimethylformamide is preferable.

As the bases, known inorganic and organic bases can be used. Examples of inorganic bases include alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), and alkali metal lower ($C_1$-$C_3$) alkoxides (e.g., sodium methoxide and sodium ethoxide). Examples of organic bases include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid form, they may also be used as a solvent.

These bases may be used singly or as a mixture of two or more. Among these, alkali metal carbonates (in particular, sodium carbonate, potassium carbonate, cesium carbonate, etc.) are preferable.

The amount of base used is generally 0.5 to 10 mol, and preferably 0.5 to 6 mol per mole of a compound represented by formula (3).

When conducting the above reaction, alkali metal iodides such as potassium iodide and sodium iodide may be added to the reaction system as reaction accelerators, if necessary.

When a reaction accelerator is used, the amount used is at least 1 mol, and preferably about 1 to 5 mol per mole of compound (4).

The proportion between compound (3) and compound (4) is generally at least 1 mol, and preferably about 1 to 5 mol of compound (4) per mole of compound (3).

The reaction temperature is not particularly limited, and the reaction may generally be conducted either under cooling, at room temperature, or under heating. The reaction is preferably conducted under temperature conditions of near room temperature to about 85° C. for 1 to 30 hours.

Compound (3')→(5):

Compound (5) can be produced by hydrolyzing compound (3').

The hydrolysis reaction of compound (3') may be conducted generally in a solvent and in the presence of a base.

The solvent is not particularly limited as long as it does not adversely affect the reaction. Examples thereof include water, alcoholic solvents (e.g., methanol, ethanol, isopropanol, and n-butanol), ketone solvents (e.g., acetone and methyl ethyl ketone), ether solvents (e.g., tetrahydrofuran, dioxane, diethylether, dimethoxyethane, and diglyme), and acetonitrile. Among these, mixed solvents of water and an alcoholic solvent (methanol or ethanol) are preferable. Alcoholic solvents (in particular, methanol and ethanol) are particularly preferable.

Examples of bases include alkali metal hydroxides (e.g., lithium hydroxide, sodium hydroxide, potassium hydroxide, and cesium hydroxide). Generally, alkali metal hydroxides can be used in the form of an aqueous solution thereof. For example, a sodium hydroxide aqueous solution may be mentioned.

The amount of base used is at least 1 mol, and preferably about 1 to 5 mol per mole of compound (3').

The reaction temperature is not particularly limited, and the reaction may generally be conducted either under cooling, at room temperature, or under heating. The reaction is preferably conducted under temperature conditions of near room temperature to about 85° C. for 1 to 30 hours.

Compound (5)→(6):

Compound (6) can be produced by subjecting compound (5) to a condensation reaction with ammonia (amidation).

The reaction may generally be conducted by reacting compound (5) with ammonia in a solvent and in the presence of a condensing agent.

The solvent is not particularly limited as long as it does not adversely affect the reaction. Examples thereof include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethylether, dimethoxyethane, and diglyme), aromatic hydrocarbons (e.g., toluene and xylene), aprotic polar solvents (e.g., acetonitrile, N,N-dimethylformamide, N-methylpyrrolidone, and dimethylsulfoxide), and mixed solvents thereof. Among these, acetonitrile is preferable.

Examples of condensing agents include 1,1'-carbonyldilmidazole (CDI), dicyclohexylcarbodiimide (DCC), diisopropylcarbodiimide (DIC), 1-ethyl-3-(3-dimethylaminopropyl)carbodiimide hydrochloride (EDC or WSC), diphenylphosphoryl azide, benzotriazol-1-yloxy-tris(dimethylamino)phosphonium salt (e.g., benzotriazol-1-yloxy-tris(dimethylamino)phosphonium hexafluorophosphate), and 2-chloro-4,6-dimethoxytriazine (CDMT). Among these, CDI is preferable.

The amount of condensing agent used is generally at least 1 mol, and preferably about 1 to 5 mol per mole of compound (5).

1-Hydroxybenzotriazole (HOBt), N-hydroxysuccinimide (HOSu) and the like may be used as an additive (activator) in combination with a condensing agent, if necessary.

When additives are used, the amount thereof is generally at least 1 mol, and preferably about 1 to 5 mol per mole of condensing agent.

The reaction may be conducted by adding a base, if necessary. Examples of bases include tertiary amines such as triethylamine and N,N-diisopropylethylamine; and nitrogen-containing aromatic compounds such as pyridine and 4-dimethylaminopyridine.

When base/bases are added, the amount thereof is generally at least 1 mol, and preferably about 1 to 5 mol per mole of compound (5).

Aqueous ammonia can generally be used as ammonia.

The amount of ammonia used is generally at least 1 mol, and preferably about 1 to 10 mol per mole of compound (5).

Typically, this reaction may be conducted by reacting compound (5) with a condensing agent and optionally an additive to prepare an active ester, and further reacting the resulting mixture with ammonia.

The reaction temperatures for the preparation of the active ester and the subsequent reaction with ammonia are not particularly limited, and either may generally be conducted under cooling, at room temperature, or under heating. Preferably, the reaction is conducted under temperature conditions of about ice cooling to room temperature for 1 to 30 hours.

Compound (6)→(8):

Compound (8) can be produced by reacting compound (6) with compound (7).

Examples of halogen atoms represented by $X^2$ include fluorine, chlorine, bromine, and iodine. Among these, chlorine, bromine, and iodine are preferable, and bromine is particularly preferable.

Examples of lower alkyl groups represented by $R^5$ include $C_1$-$C_6$ (in particular, $C_1$-$C_3$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl and ethyl are preferable.

The reaction can generally be conducted in the presence of a solvent. The solvent is not particularly limited as long as it does not adversely affect the reaction. Examples thereof include water, alcoholic solvents (e.g., methanol, ethanol, isopropanol, n-butanol, trifluoroethanol, and ethylene glycol), ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, alcoholic solvents (in particular, methanol and ethanol) are preferable.

The proportion between compound (6) and compound (7) is generally at least 1 mol, and preferably about 1 to 5 mol of the latter per mole of the former.

The reaction temperature is not particularly limited, and the reaction may generally be conducted under cooling, at room temperature, or under heating. The reaction is preferably conducted under temperature conditions of near-room temperature to about 85° C. for 1 to 30 hours.

Alternatively, compound (8) can be produced by reacting compound (6) with pyruvic acid ester (21) and a halogenating agent. It is believed that compound (7) is once generated by a reaction between pyruvic acid ester (21) and a halogenating agent, and the resulting product is reacted with compound (6) to produce compound (8). Compound (7) generated by a reaction between pyruvic acid ester (21) and a halogenating agent can be reacted with compound (6) with or without isolating.

The reaction can generally be conducted in a solvent that does not adversely affect the reaction. Examples of solvents include those used in the reaction between compound (6) and compound (7) described above.

Examples of halogenating agents include halogens ($X^2_2$: wherein $X^2$ is a halogen atom, such as chlorine, bromine, and iodine), and N-halosuccinimides (e.g., N-chlorosuccinimide, N-bromosuccinimide, N-iodosuccinimide, etc.). Among these, bromine is preferable.

The proportion between compound (6) and pyruvic acid ester (21) is generally at least 1 mol and preferably about 1 to 5 mol of the latter per mole of the former.

The proportion between pyruvic acid ester (21) and the halogenating agent is generally at least 1 mol and preferably about 1 to 5 mol of the latter per mole of the former.

The reaction temperature is not particularly limited, and may generally be conducted under cooling, at room temperature, or under heating. Preferably, the reaction is conducted under temperature conditions of near room temperature to about the boiling point of the solvent for 1 to 30 hours.

Compound (8)→(9):

Compound (9) can be produced by debenzylating compound (8).

The reaction can generally be conducted in the presence of a solvent. The solvent is not particularly limited as long as it does not adversely affect the reaction. Examples of solvents include water, alcoholic solvents (e.g., methanol, ethanol, isopropanol, n-butanol, trifluoroethanol, and ethylene glycol), aprotic polar solvents (e.g., amide solvents such as N,N-dimethylformamide and N,N-dimethylacetamide), and mixed solvents thereof. Among these, alcoholic solvents (e.g., methanol and ethanol) are preferable.

Examples of catalysts suitable for the debenzylation reaction include platinum catalysts (e.g., platinum plate, spongy platinum, platinum black, colloidal platinum, platinum oxide, and platinum wire), palladium catalysts (e.g., spongy palladium, palladium black, palladium oxide, palladium carbon, palladium/barium sulfate, and palladium/barium carbonate), nickel catalysts (e.g., reduced nickel, nickel oxide, and Raney nickel), cobalt catalysts (e.g., reduced cobalt and Raney cobalt), and iron catalysts (e.g., reduced iron). Among these, palladium catalysts (in particular, palladium black, palladium oxide, and palladium carbon) are preferable.

The amount of catalyst used for the debenzylation reaction is not particularly limited, and is preferably, for example, 5 to 10 parts by weight per 100 parts by weight of compound (8).

The reaction is conducted in a hydrogen atmosphere wherein the pressure of hydrogen is generally about 0.1 to 0.5 MPa.

The reaction temperature is generally about 0 to 120° C., and the reaction time is generally about 30 minutes to 24 hours.

Compounds (9)+(10)→(11):

Compound (11) can be produced by reacting compound (9) with compound (10) in the presence of a base.

Examples of lower alkyl groups represented by $R^{11}$ include $C_1$-$C_6$ (in particular, $C_1$-$C_4$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl and ethyl are preferable.

Examples of halogen substituted lower alkyl groups represented by $R^{11}$ include lower alkyl groups in which at least one (preferably, 1 to 7, in particular 1 to 3) hydrogen atoms bonded to a carbon atom of the lower alkyl groups as above is/are substituted with halogen atom(s). Specific examples thereof include fluoromethyl, chloromethyl, bromomethyl, iodomethyl, difluoromethyl, dichloromethyl, trifluoromethyl, chlorodifluoromethyl, bromodifluoromethyl, trichloromethyl, 2-fluoroethyl, 2-chloroethyl, 2-bromoethyl, 2,2-difluoroethyl, 2,2,2-trifluoroethyl, pentafluoroethyl, heptafluoropropyl, and heptafluoroisopropyl. Among these, difluoromethyl is preferable.

In the formula: —$CY_2COOR^{12}$ represented by $R^{11}$, wherein Y is a halogen atom, and $R^{12}$ is an alkali metal atom or a lower alkyl, examples of halogen atoms represented by Y include fluorine and chlorine. Among these, fluorine is preferable. Examples of alkali metal atoms represented by $R^{12}$ include lithium, sodium, and potassium. Among these, sodium is preferable. Examples of lower alkyl groups represented by $R^{12}$ include $C_1$-$C_6$ (in particular, $C_1$-$C_4$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl and ethyl are preferable.

Examples of groups represented by the formula above include —$CF_2COONa$, —$CCl_2COONa$, —$CF_2COOCH_3$, and —$CF_2COOCH_2CH_3$.

Examples of lower alkyl groups and halogen substituted lower alkyl groups represented by $R^1$ include the lower alkyl groups and halogen substituted lower alkyl groups represented by $R^{11}$ described above.

Examples of halogen atoms represented by $X^3$ include fluorine, chlorine, bromine, and iodine. Among these, chlorine, bromine, and iodine are preferable.

The reaction can generally be conducted in the presence of a solvent. The solvent is not particularly limited as long as it does not adversely affect the reaction. Examples of solvents include ketone solvents (e.g., acetone and methyl ethyl ketone), ether solvents (e.g., tetrahydrofuran, dioxane, diethylether, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, N,N-dimethylformamide is preferable.

As the bases, known inorganic and organic bases can be used. Examples of inorganic bases include alkali metals (e.g., sodium and potassium), alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower ($C_1$-$C_3$)

alkoxides (e.g., sodium methoxide and sodium ethoxide), and alkali metal hydrides (e.g., sodium hydride and potassium hydride). Examples of organic bases include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid form, they may also be used as a solvent. These bases may be used singly or as a mixture of two or more. The bases are preferably alkali metal carbonates (in particular, sodium carbonate and potassium carbonate).

The amount of base used is generally 1 to 10 mol, and preferably 1 to 6 mol per mole of compound (9).

When conducting the above reaction, alkali metal iodides, such as potassium iodide and sodium iodide, may be added to the reaction system as reaction accelerators, if necessary.

When a reaction accelerator is used, the amount used is at least 1 mol, and preferably about 1 to 5 mol per mole of compound (10).

The proportion between compound (9) and compound (10) is generally at least 1 mol, and preferably about 1 to 5 mol of the latter per mole of the former.

The reaction temperature is not particularly limited, and the reaction may generally be conducted either under cooling, at room temperature, or under heating. The reaction is preferably conducted under temperature conditions of near room temperature to about 85° C. for 1 to 30 hours.

Compound (11)→(12):

Compound (12) can be produced by reducing compound (11).

The reaction is generally conducted by reacting compound (11) with a reducing agent in a solvent.

The solvent is not particularly limited as long as it does not adversely affect the reaction. Examples thereof include ether solvents (e.g., tetrahydrofuran, dioxane, diethylether, dimethoxyethane, and diglyme), alcoholic solvents (e.g., methanol, ethanol, isopropanol, n-butanol, trifluoroethanol, and ethylene glycol), and mixed solvents thereof. Among these, ether solvents (in particular, dimethoxyethane) are preferable.

Examples of reducing agents include hydride reducing agents. Specific examples thereof include sodium borohydride, zinc borohydride ($Zn(BH_4)_2$), tetramethylammonium triacetoxyborohydride, lithium tri(sec-butyl)borohydride, borane, borane.THF complex, borane.dimethylsulfide complex, and lithium aluminium hydride. Among these, zinc borohydride, borane, borane.THF complex, borane.dimethylsulfide complex, and lithium aluminium hydride are preferable, and zinc borohydride is particularly preferable.

The amount of reducing agent used is generally 0.5 to 10 mol, and preferably 0.5 to 6 mol per mole of compound (11).

Among the above reducing agents, zinc borohydride can generally be prepared using sodium borohydride and zinc halide ($ZnX^5_2$: wherein $X^5$ is a halogen atom, such as chlorine and bromine). The proportion of zinc halide and sodium borohydride is generally 1 to 5 mol, preferably 1.5 to 2.5 mol, and particularly preferably about 2 mol of the latter per mole of the former. The amount of zinc halide used is generally 0.5 to 10 mol, and preferably 0.5 to 6 mol per mole of compound (11).

The reaction temperature is not particularly limited, and the reaction may generally be conducted under cooling, at room temperature, or under heating. Preferably, the reaction is conducted under temperature conditions of near room temperature to about 100° C. for 1 to 30 hours.

Compound (12)→(13):

Compound (13) can be produced by converting the hydroxy group of compound (12) into a leaving group ($X^4$).

Examples of leaving groups represented by $X^4$ include halogen atoms (e.g., fluorine, chlorine, bromine, and iodine), and organic sulfonyloxy groups (e.g., p-toluenesulfonyloxy, methanesulfonyloxy, trifluoromethanesulfonyloxy, nonafluorobutanesulfonyloxy, and o-nitrobenzenesulfonyloxy). Among these, halogen atom is preferable, and bromine is particularly preferable.

In the case of compound (13') wherein the leaving group represented by $X^4$ is an organic sulfonyloxy group, compound (13') can be produced by reacting compound (12), in a solvent and in the presence of a base, with organic sulfonyl halide or organic sulfonyl anhydride containing organic sulfonyl group.

The solvent is not particularly limited as long as it does not adversely affect the reaction. Examples thereof include ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, ester solvents (in particular, ethyl acetate, etc.) are preferable.

As the bases, known inorganic and organic bases can be used. Examples of inorganic bases include alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), and alkali metal hydrides (e.g., sodium hydride and potassium hydride). Examples of organic bases include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid form, they may also be used as a solvent. These bases may be used singly or as a mixture of two or more. Among these, triethylamine is preferable.

Examples of organic sulfonyl halides include p-toluenesulfonyl halide, methanesulfonyl halide, trifluoromethanesulfonyl halide, nonafluorobutanesulfonyl halide, and o-nitrobenzenesulfonyl halide. Specific examples of halides include chloride, and bromide. Among these, chloride is preferable.

Examples of organic sulfonyl anhydrides include p-toluenesulfonic anhydride, methanesulfonic anhydride, trifluorosulfonic anhydride, nonafluorobutanesulfonic anhydride, and o-nitrobenzenesulfonic anhydride.

The amount of base used is generally 1 to 10 mol, and preferably 1 to 6 mol per mole of compound (12).

The amount of organic sulfonyl halide or organic sulfonyl anhydride used is generally 1 to 5 mol, and preferably 1 to 2 mol per mole of compound (12).

The reaction temperature is not particularly limited, and the reaction may generally be conducted under cooling, at room temperature, or under heating. The reaction is preferably conducted under temperature conditions of about 0 to 60° C. for 1 to 30 hours.

Compound (13'), wherein the leaving group represented by $X^4$ is an organic sulfonyloxy group, can be produced by the above-described reaction.

Compound (13"), wherein the leaving group represented by $X^4$ is a halogen atom, can be produced by reacting a halogenating agent with compound (13') in a solvent.

The solvent is not particularly limited as long as it does not adversely affect the reaction. Examples thereof include ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof.

Examples of halogenating agents include alkali metal halides (e.g., lithium chloride, lithium bromide, lithium iodide, etc.), and quaternary ammonium halides (e.g., tetrabutylammonium chloride and tetrabutylammonium bromide). Among these, alkali metal halides (in particular, lithium bromide) are preferable.

The amount of halogenating agent used is generally 1 to 5 mol, and preferably 1 to 3 mol per mole of compound (13').

The reaction temperature is not particularly limited, and the reaction may generally be conducted under cooling, at room temperature, or under heating. The reaction is preferably conducted under temperature conditions of about 0 to 60° C. for 1 to 30 hours.

The process of producing compound (13') from compound (12) and the process of producing compound (13") from the resulting compound (13') may be conducted independently, or both may be conducted as a one-pot process.

The compound (13) (including compound (13') and compound (13")) thus obtained may be supplied to the subsequent reaction process.

Compounds (13)+(14)→(15):

Compound (15) can be produced by reacting compound (13) with compound (14).

Examples of alkali metal atoms represented by M include lithium, sodium, and potassium. Among these, potassium is preferable.

The reaction may generally be conducted in a solvent. The solvent is not particularly limited as long as it does not adversely affect the reaction. Examples thereof include ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, N,N-dimethylformamide is particularly preferable.

The proportion of compound (13) and compound (14) used is generally at least 1 mol, and preferably about 1 to 5 mol of the latter per mole of the former.

The reaction temperature is not particularly limited, and the reaction may generally be conducted under cooling, at room temperature, or under heating. The reaction is preferably conducted under temperature conditions of about 0 to 100° C. for 1 to 30 hours.

Compound (15)→(16):

Compound (16) can be produced by reacting compound (15) with methylamine.

The reaction may generally be conducted in a solvent. The solvent is not particularly limited as long as it does not adversely affect the reaction. Examples thereof include water, alcoholic solvents (e.g., methanol, ethanol, isopropanol, n-butanol, trifluoroethanol, and ethylene glycol), ether solvents (e.g., tetrahydrofuran, dioxane, diethylether, dimethoxyethane, and diglyme), aprotic polar solvents (e.g., acetonitrile, N,N-dimethylformamide, and dimethylsulfoxide), and mixed solvents thereof. Among these, mixed solvents of water and alcoholic solvents (in particular, methanol or ethanol) are preferable.

Generally, methylamine can be used in the form of an aqueous solution of methylamine.

The amount of methylamine used is generally 1 to 10 mol, and preferably 1 to 5 mol per mole of compound (15).

The reaction temperature is not particularly limited, and the reaction may generally be conducted under cooling, at room temperature, or under heating. The reaction is preferably conducted under temperature conditions of near room temperature to about 100° C. for 10 minutes to 30 hours.

The resulting compound (16) is a primary amine compound. From the viewpoint of handleability, compound (16) may be converted with an acid into a salt, if necessary. Formation of a salt can be performed using a publicly known method. The acid used may be selected from a wide variety of organic or inorganic acids. Examples of organic acids include organic carboxylic acids such as formic acid, acetic acid, lactic acid, tartaric acid, and succinic acid; and sulfonic acids such as methanesulfonic acid, toluenesulfonic acid, and naphthalenesulfonic acid. Examples of inorganic acids include hydrochloric acid, sulfuric acid, nitric acid, and phosphoric acid.

Compound (16)+(17)→(1):

Compound (1) can be produced by subjecting compound (16) to a condensation reaction with compound (17) or compound (17').

When $Ar^1$ is phenyl substituted with at least one substituent selected from the group consisting of lower alkyl group, halogen substituted lower alkyl group, lower alkoxy group and halogen substituted lower alkoxy group, examples of alkyl groups include $C_1$-$C_4$ alkyl groups such as methyl, ethyl, n-propyl, isopropyl, n-butyl, isobutyl, sec-butyl, and tert-butyl. Among these, methyl and ethyl are preferable.

Examples of halogen substituted lower alkyl groups include halogen substituted $C_1$-$C_4$ alkyl groups such as fluoromethyl, difluoromethyl, trifluoromethyl, and 2,2,2-trifluoroethyl. Among these, difluoromethyl and trifluoromethyl are preferable.

Examples of lower alkoxy groups include $C_1$-$C_4$ alkoxy such as methoxy, ethoxy, n-propoxy, isopropoxy, n-butyloxy, isobutyloxy, sec-butyloxy, and tert-butyloxy. Among these, methoxy and ethoxy are preferable.

Examples of halogen substituted lower alkoxy groups include halogen substituted $C_1$-$C_4$ alkoxy groups such as fluoromethoxy, difluoromethoxy, trifluoromethoxy, and 2,2,2-trifluoroethoxy. Among these, difluoromethoxy is preferable.

Phenyl group has 1 to 3 (preferably, 1) substituents selected from the group consisting of the above-mentioned substituents.

Specific examples of the substituted phenyl group represented by $Ar^1$ include lower alkylphenyl groups (e.g., 2-methylphenyl and 2-ethylphenyl), halogen substituted lower alkylphenyl groups (e.g., 2-fluoromethylphenyl, 2-difluoromethylphenyl, and 2-trifluoromethylphenyl), lower alkoxyphenyl groups (e.g., 2-methoxyphenyl and 2-ethoxyphenyl), and halogen substituted lower alkoxyphenyl groups (e.g., 2-fluoromethoxyphenyl, 2-difluoromethoxyphenyl, and 2-trifluoromethoxyphenyl). Among these, 2-methylphenyl, 2-difluoromethoxyphenyl, and 2-ethoxyphenyl are preferable.

When Ar$^1$ is pyridyl group substituted with at least one substituent selected from the group consisting of lower alkyl group, halogen substituted lower alkyl group, lower alkoxy group and halogen substituted lower alkoxy group, examples of lower alkyl groups include $C_1$-$C_4$ alkyl groups such as methyl, ethyl, n-propyl, isopropyl, n-butyl, isobutyl, sec-butyl, and tert-butyl. Among these, methyl and ethyl are preferable.

Examples of halogen substituted lower alkyl groups include halogen substituted $C_1$-$C_4$ alkyl groups such as fluoromethyl, difluoromethyl, trifluoromethyl, and 2,2,2-trifluoroethyl. Among these, difluoromethyl and trifluoromethyl are preferable.

Examples of lower alkoxy groups include $C_1$-$C_4$ alkoxy groups such as methoxy, ethoxy, n-propoxy, isopropoxy, n-butyloxy, isobutyloxy, sec-butyloxy, and tert-butyloxy. Among these, methoxy and ethoxy are preferable.

Examples of halogen substituted lower alkoxy groups include halogen substituted $C_1$-$C_4$ alkoxy groups such as fluoromethoxy, difluoromethoxy, trifluoromethoxy, and 2,2,2-trifluoroethoxy. Among these, difluoromethoxy is preferable.

Pyridyl group has 1 to 3 (preferably, 1) substituents selected from the group consisting of above-mentioned substituents.

Specific examples of the substituted-pyridyl groups represented by Ar$^1$ include lower alkylpyridyl groups (e.g., 3-methylpyridin-2-ly and 3-ethylpyridin-2-ly), halogen substituted lower alkylpyridyl groups (e.g., 3-fluoromethylpyridin-2-ly, 3-difluoromethylpyridin-2-ly, and 3-trifluoromethylpyridin-2-ly), lower alkoxypyridyl groups (e.g., 3-methoxypyridin-2-ly and 3-ethoxypyridin-2-ly), and halogen substituted lower alkoxypyridyl groups (e.g., 3-fluoromethoxypyridin-2-ly, 3-difluoromethoxypyridin-2-ly, and 3-trifluoromethoxypyridin-2-ly). Among these, 3-methylpyridin-2-ly is preferable.

The reaction between compound (16) and compound (17) may generally be conducted in a solvent and in the presence of a condensing agent. When compound (16) forms a salt with an acid, the reaction may be conducted after removing the acid from the salt to convert the salt into compound (16), which is a free primary amine, using a base. (Examples of usable bases include inorganic bases such as sodium hydroxide, potassium hydroxide, sodium carbonate, and sodium hydrogencarbonate; and organic bases such as triethylamine, N,N-diisopropylethylamine.)

The solvent is not particularly limited as long as it does not adversely affect the reaction. Examples thereof include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethylether, dimethoxyethane, and diglyme), aromatic hydrocarbons (e.g., toluene and xylene), aprotic polar solvents (e.g., acetonitrile, N,N-dimethylformamide, N-methylpyrrolidone, and dimethylsulfoxide), and mixed solvents thereof. Among these, ketone solvents (in particular, acetone and methyl ethyl ketone) and ether solvents (in particular, tetrahydrofuran, dioxane, diethylether, and dimethoxyethane) are preferable.

Examples of condensing agents include 1,1'-carbonyldiimidazole (CDI), dicyclohexylcarbodiimide (DCC), diisopropylcarbodiimide (DIC), 1-ethyl-3-(3-dimethylaminopropyl)carbodiimide hydrochloride (EDC or WSC), diphenylphosphoryl azide, benzotriazol-1-yloxy-tris(dimethylamino)phosphonium salt (e.g., benzotriazol-1-yloxy-tris(dimethylamino)phosphonium hexafluorophosphate), and 2-chloro-4,6-dimethoxytriazine (CDMT). Among these, CDI and EDC are preferable.

The amount of the condensing agent used is generally at least 1 mol, and preferably about 1 to 5 mol per mole of compound (17).

1-Hydroxybenzotriazole (HOBt), N-hydroxysuccinimide (HOSu), and the like may be used as an additive (activator) in combination with a condensing agent, if necessary.

The amount thereof is generally at least 1 mol and preferably about 1 to 5 mol per mole of condensing agent.

The reaction may be conducted by adding a base, if necessary. Examples of the usable bases include tertiary amines such as triethylamine and N,N-diisopropylethylamine; and nitrogen-containing aromatic compounds such as pyridine and 4-dimethylaminopyridine.

When one or more bases are used, the amount thereof is generally at least 1 mol, and preferably about 1 to 5 mol per mole of the condensing agent.

The proportion between compound (16) and compound (17) is generally at least 1 mol, and preferably about 1 to 2 mol of the latter per mole of the former.

The reaction temperature is not particularly limited, and the reaction may generally be conducted under cooling, at room temperature, or under heating. The reaction is preferably conducted under the temperature conditions of about 0 to 100° C. for 1 to 30 hours.

The reaction between compound (16) and compound (17') is generally conducted in a solvent and in the presence of a base.

The solvent is not particularly limited, as long as it does not adversely affect the reaction. Examples thereof include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aromatic hydrocarbons (e.g., toluene and xylene), aprotic polar solvents (e.g., acetonitrile, N,N-dimethylformamide, N-methylpyrrolidone, and dimethylsulfoxide), and mixed solvents thereof. Among these, ester solvents (e.g., ethyl acetate), ketone solvents (in particular, acetone and methyl ethyl ketone); and ether solvents (in particular, tetrahydrofuran, dioxane, diethylether, and dimethoxyethane) are preferable.

Examples of bases include inorganic bases such as sodium hydroxide, potassium hydroxide, sodium carbonate, and sodium hydrogen carbonate; and organic bases such as trimethylamine, N,N-diisopropylethylamine, pyridine, and 4-dimethylaminopyridine.

The amount of base used is generally at least 1 mol, and preferably about 1 to 5 mol per mole of compound (17').

The proportion between compound (16) and compound (17') is generally at least 1 mol, and preferably about 1.2 to 2 mol of the latter per mole of the former.

The reaction temperature is not particularly limited, and the reaction may generally be conducted either under cooling, at room temperature, or under heating. The reaction is preferably conducted under temperature conditions of about 0 to 100° C. for 1 to 30 hours.

The compound (17') can be obtained from compound (17) by a known method. For example, compound (17') can be produced by reacting compound (17) with a halogenating agent (e.g., thionyl chloride, sulfuryl chloride, oxalyl chloride, phosphorus trichloride, silicon tetrachloride, phosgene, triphosgene, thionyl bromide, phosphorus tribromide, triphenylphosphine dibromide) with in a solvent (e.g., ethyl acetate, toluene, dichloromethane, chlorobenzene). In order to promote the reaction, additives (e.g., DMF, DMA, and NMP) may be added, if necessary.

All compounds (11), (12), (13), (15), and (16) in Reaction Scheme 1 can be collectively shown in formula (A) below:

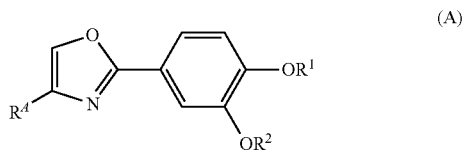

(A)

wherein $R^A$ is a group represented by formula: $-COOR^5$, $-CH_2OH$, $-CH_2X^4$, 1,3-dioxoisoindolin-2-ylmethyl, or $-CH_2NH_2$; and $R^1$, $R^2$, $R^5$, and $X^4$ are as defined above.

The intermediate compound (12) shown in Reaction Scheme 1 can be separately produced in the procedure shown in Reaction Scheme 2 below.

wherein $R^7$ is alkanoyl, $X^8$ is a halogen atom, and other symbols are as defined above.

Compound (3')→(29):

Compound (29) can be produced by debenzylating compound (3'). The reaction can be conducted by or based on the conditions for the reaction of compound (8)→(9) in Reaction Scheme 1.

Compound (29)→(30):

Compound (30) can be produced by reacting compound (29) with compound (10) in the presence of a base. The reaction can be conducted by or based on the conditions for the reaction of compound (9)+(10)→(11) in Reaction Scheme 1.

Compound (30)→(31):

Compound (31) can be produced by hydrolyzing compound (30). The reaction can be conducted by or based on the conditions for the reaction of compound (3')→(5) in Reaction Scheme 1. The process producing compound (31) from compound (29) through compound (30) can be conducted as a one-pot process.

Reaction Scheme 2

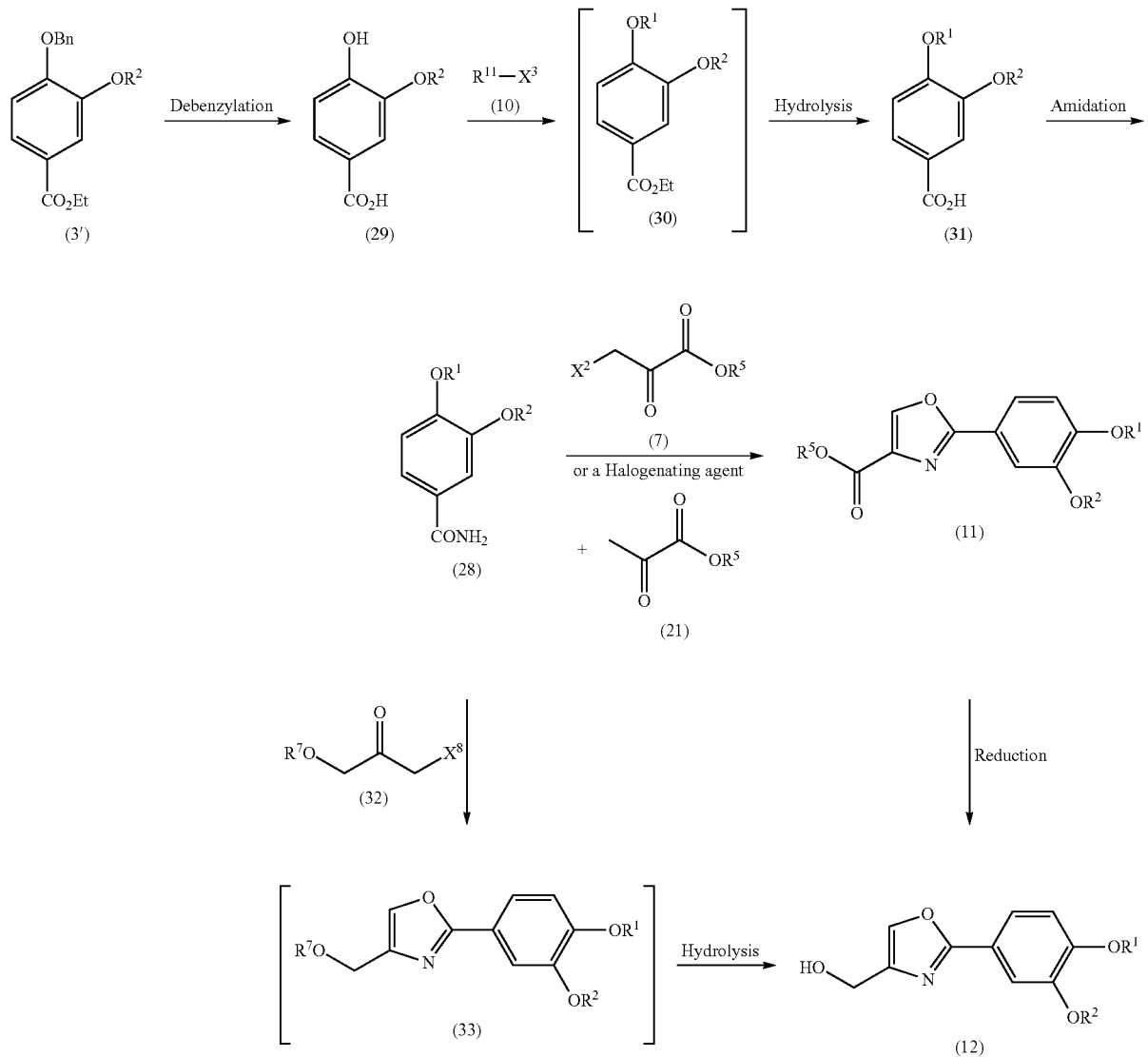

Compound (31)→(28):

Compound (28) can be produced by subjecting compound (31) to a condensation reaction with ammonia (amidation). The reaction can be conducted by or based on the conditions for the reaction of compound (5)→(6) in Reaction Scheme 1.

Compound (28)→(11):

The reaction producing compound (11) from compound (28) can be conducted by or based on the conditions for the reaction of compound (6)→(8) in Reaction Scheme 1.

Compound (11)→(12):

The reaction can be conducted by or based on the conditions for the reaction of compound (11)→(12) in Reaction Scheme 1.

Compound (28)+(32)→(33):

Compound (33) can be produced by reacting compound (28) with compound (32).

Examples of the alkanoyl groups represented by $R^7$ include $C_1$-$C_6$ (in particular, $C_1$-$C_4$) linear or branched alkanoyl groups. Specific examples thereof include formyl, acetyl, n-propionyl, isopropionyl, n-butyryl, isobutyryl, sec-butyryl, tert-butyryl, and hexanoyl. Among these, formyl, acetyl, n-propionyl, and isopropionyl are preferable, and acetyl is particularly preferable.

Examples of halogen atoms represented by $X^8$ include fluorine, chlorine, bromine, and iodine. Among these, chlorine, bromine, and iodine are preferable.

The reaction can generally be conducted in the presence of a solvent. The solvent is not particularly limited as long as it does not adversely affect the reaction. Examples of solvents include halogenated aliphatic hydrocarbon solvents (e.g., methylene chloride, chloroform, and ethylene chloride), ketone solvents (e.g., acetone and methyl ethyl ketone), ether solvents (e.g., tetrahydrofuran, dioxane, diethylether, dimethoxyethane, and diglyme), aromatic hydrocarbons (e.g., toluene and xylene), aprotic polar solvents (e.g., acetonitrile, N,N-dimethylformamide, N-methylpyrrolidone, and dimethylsulfoxide), and mixed solvents thereof. Among these, aromatic hydrocarbons (e.g., toluene and xylene) are preferable.

The proportion between compound (28) and compound (32) is generally at least 1 mol, and preferably about 1 to 5 mol of the latter per mole of the former.

Dehydrating agents may be added thereto, if necessary. Examples of the usable dehydrating agents include synthetic zeolites. Specific examples thereof include Molecular Sieves (MS) 3A, MS 4A, or zeolites having pores similar thereto.

The reaction temperature is not particularly limited, and the reaction may generally be conducted either under cooling, at room temperature, or under heating. The reaction is preferably conducted under the temperature conditions of about room temperature to 200° C. for 1 to 30 hours. This allows the formation of an oxazole ring at a high yield.

Compound (33)→(12):

Compound (12) can be produced by hydrolyzing compound (33). The hydrolysis reaction can be conducted by or based on the conditions for the reaction of compound (3')→(5) in Reaction Scheme 1. The process to produce compound (12) from compound (28) through compound (33) can also be conducted as a one-pot process.

It is also possible to lead compound (12) obtained by the method described above to compound (1) based on Reaction Scheme 1.

In each compound in Reaction Scheme 1 and Reaction Scheme 2, $R^1$ is preferably methyl or difluoromethyl, and $R^2$ is preferably methyl, isopropyl, or isobutyl.

Among the intermediate compounds represented by formula (12), a preferable compound is such that $R^1$ is methyl, or difluoromethyl, and $R^2$ is methyl, isopropyl, or isobutyl. More specifically, the preferable compound is represented by formula (12A):

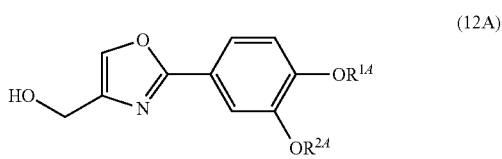

(12A)

wherein $R^{1A}$ is methyl or difluoromethyl, $R^{2A}$ is methyl, isopropyl, or isobutyl.

In particular, when $R^{1A}$ is methyl, $R^{2A}$ is preferably isopropyl, or isobutyl, and when $R^{1A}$ is difluoromethyl, $R^{2A}$ is preferably methyl, isopropyl or isobutyl.

In each step in Reaction Scheme 1 and Reaction Scheme 2, after completion of the reaction, the target compound can be obtained from the reaction mixture by a known isolation operation (such as filtration, concentration, or extraction). The method of the present invention does not use 1,3-dihaloacetone and hydrazine, which are required in the method of Patent Literature 1, and allows the target product to be produced in a simple and effective manner without using column chromatography throughout the production processes thereof.

Reaction Scheme 2 is desirable as a process for the industrial-scale production of a compound represented by formula (1) because it enables the efficient formation of an oxazole ring midway through a series of reaction processes.

2. Production of Compound Represented by Formula (2)

The compound represented by formula (2) can be produced through the reaction steps shown in Reaction Scheme 3.

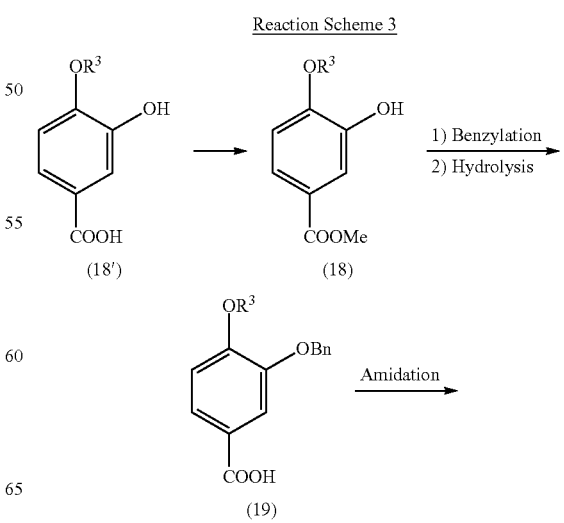

Reaction Scheme 3

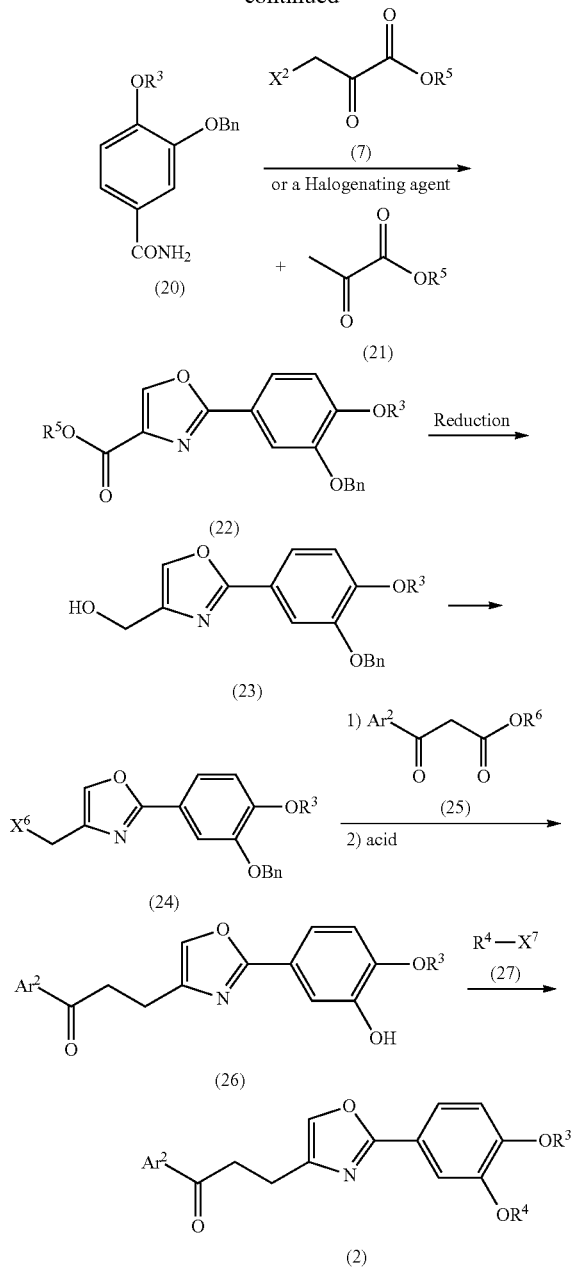

wherein $R^3$ is lower alkyl group or halogen substituted lower alkyl group; $R^4$ is lower alkyl group, cycloalkyl-lower alkyl group or lower alkenyl group; $R^6$ is lower alkyl group; $Ar^2$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group; $X^6$ is a leaving group; $X^7$ is a halogen atom; and $R^5$ and $X^2$ are as defined above.

Synthesis of Compound (18)

Ester compound (18) can be produced by esterifying (methyl esterifying) carboxylic acid compound (18') by a known method.

Examples of lower alkyl groups represented by $R^3$ include $C_1$-$C_6$ (in particular, $C_1$-$C_4$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl, ethyl, isopropyl, and isobutyl are preferable, methyl and ethyl are more preferable, and methyl is particularly preferable.

Examples of halogen substituted lower alkyl groups represented by $R^3$ include lower alkyl groups in which at least one (preferably, 1 to 7, in particular 1 to 3) hydrogen atoms bonded to a carbon atom of the lower alkyl groups as above is/are substituted with halogen atom(s).

Specific examples thereof include fluoromethyl, chloromethyl, bromomethyl, iodomethyl, difluoromethyl, dichloromethyl, trifluoromethyl, chlorodifluoromethyl, bromodifluoromethyl, trichloromethyl, 2-fluoroethyl, 2-chloroethyl, 2-bromoethyl, 2,2-difluoroethyl, 2,2,2-trifluoroethyl, pentafluoroethyl, heptafluoropropyl, and heptafluoroisopropyl. Among these, difluoromethyl is preferable.

The reaction described above may be conducted by, for example, reacting carboxylic acid compound (18') with methanol in the presence of an acid (e.g., p-toluenesulfonic acid) to obtain ester compound (18). The reaction may also be conducted by reacting carboxylic acid compound (18') with a halogenating agent (e.g., thionyl chloride) to obtain a carboxylic acid halide, and reacting the carboxylic acid halide with methanol to obtain ester compound (18). These reactions may be easily conducted by a person of skill in the art based on a known method.

Compound (18)→(19):

Compound (19) can be produced by converting the hydroxyl group of compound (18) into benzyloxy group (benzylation), and hydrolyzing the ester (methyl ester).

The benzylation described above can generally be conducted by reacting compound (18) with benzyl halide in a solvent and in the presence of a base.

The solvent is not particularly limited, as long as it does not adversely affect the reaction. Examples thereof include water, alcoholic solvents (e.g., methanol, ethanol, isopropanol, n-butanol), ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aromatic hydrocarbons (e.g., toluene and xylene), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof.

As the bases, known inorganic and organic bases can be used. Examples of inorganic bases include alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), and alkali metal lower ($C_1$-$C_3$) alkoxides (e.g., sodium methoxide and sodium ethoxide). Examples of organic bases include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid form, they may also be used as a solvent. These bases may be used singly or as a mixture of two or more.

The amount of base used is generally 0.5 to 10 mol, and preferably 0.5 to 6 mol per mole of compound (18).

In order to promote the reaction, a phase transfer catalyst may be added. Examples of phase transfer catalysts include quaternary ammonium salts, such as tetrabutylammonium fluoride (TBAF), tetrabutylammonium chloride (TBAC), and tetrabutylammonium bromide (TBAB).

When a phase transfer catalyst is used, the amount thereof is generally 0.01 to 0.5 mol, and preferably 0.05 to 0.3 mol per mole of compound (18).

Examples of benzyl halides include benzyl chloride, benzyl bromide, and benzyl iodide.

The proportion between compound (18) and benzyl halide is generally at least 1 mol, and preferably about 1 to 5 mol of the latter per mole of the former.

The reaction temperature is not particularly limited, and the reaction may generally be conducted under cooling, at room temperature, or under heating. The reaction is preferably conducted under the temperature conditions of about 0 to 100° C. for 1 to 30 hours.

The hydrolysis reaction can be conducted by or based on the conditions for the reaction of compound (3')→(5) in Reaction Scheme 1.

Compound (19)→(20):

Compound (20) can be produced by subjecting compound (19) to a condensation reaction with ammonia (amidation). The reaction can be conducted by or based on the conditions for the reaction of compound (5)→(6) in Reaction Scheme 1.

Compound (20)→(22):

Compound (22) can be produced by reacting compound (20) with compound (7). More specifically, it can be produced by reacting compound (20) with compound (7), or by reacting compound (20) with pyruvic acid ester (21) and a halogenating agent. The reaction can be conducted by or based on the conditions for the reaction of compound (6)→(8) in Reaction Scheme 1.

Compound (22)→(23):

Compound (23) can be produced by reducing compound (22). The reaction can be conducted by or based on the conditions for the reaction of compound (11)→(12) in Reaction Scheme 1.

Compound (23)→(24):

Compound (24) can be produced by converting the hydroxyl group of compound (23) to a leaving group ($X^6$).

Examples of leaving groups represented by $X^6$ include halogen atoms (e.g., fluorine, chlorine, bromine, and iodine), and organic sulfonyloxy groups (e.g., p-toluenesulfonyloxy, methanesulfonyloxy, trifluoromethanesulfonyloxy, nonafluorobutanesulfonyloxy, and o-nitrobenzenesulfonyloxy). Among these, halogen atoms are preferable, and bromine is particularly preferable.

The reaction can be conducted by or based on the conditions for the reaction of compound (12)→(13) in Reaction Scheme 1. More specifically, in the case of compound (24') whose leaving group ($X^6$) is organic sulfonyloxy, the reaction can be conducted by or based on the reaction for producing compound (13'); and in the case of compound (24") whose leaving group ($X^6$) is a halogen atom, the reaction can be conducted by or based on the reaction for producing compound (13").

Compound (24)+(25)→(26):

Compound (26) can be produced by reacting compound (24) with compound (25) and then treating the resultant with an acid.

Examples of lower alkyl groups represented by $R^6$ include $C_1$-$C_6$ (in particular, $C_1$-$C_3$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl and ethyl are preferable.

When the substituent represented by $Ar^2$ is phenyl group substituted with at least one substituent selected from the group consisting of lower alkyl group, halogen substituted lower alkyl group, lower alkoxy group and halogen substituted lower alkoxy group, examples of lower alkyl groups include $C_1$-$C_4$ alkyl groups such as methyl, ethyl, n-propyl, isopropyl, n-butyl, isobutyl, sec-butyl, and tert-butyl. Among these, methyl and ethyl are preferable.

Examples of halogen substituted lower alkyl groups include halogen substituted $C_1$-$C_4$ alkyl groups such as fluoromethyl, difluoromethyl, trifluoromethyl, and 2,2,2-trifluoroethyl. Among these, difluoromethyl is preferable.

Examples of lower alkoxy groups include $C_1$-$C_4$ alkoxy groups such as methoxy, ethoxy, n-propoxy, isopropoxy, n-butyloxy, isobutyloxy, sec-butyloxy, and tert-butyloxy. Among these, methoxy and ethoxy are preferable.

Examples of halogen substituted lower alkoxy groups include halogen substituted $C_1$-$C_4$ alkoxy groups such as fluoromethoxy, difluoromethoxy, trifluoromethoxy, and 2,2,2-trifluoroethoxy.

Phenyl group has 1 to 3 (preferably, 1) substituents selected from the above-mentioned substituents.

Specific examples of the substituted-phenyl group represented by $Ar^2$ include lower alkylphenyl groups (e.g., 2-methylphenyl and 2-ethylphenyl), halogen substituted lower alkylphenyl groups (e.g., 2-fluoromethylphenyl, 2-difluoromethylphenyl, and 2-trifluoromethylphenyl), lower alkoxyphenyl groups (e.g., 2-methoxyphenyl and 2-ethoxyphenyl), and halogen substituted lower alkoxyphenyl groups (e.g., 2-fluoromethoxyphenyl, 2-difluoromethoxyphenyl, and 2-trifluoromethoxyphenyl). Among these, 2-methylphenyl, 2-difluoromethoxyphenyl, and 2-ethoxyphenyl are preferable.

When the substituent represented by $Ar^2$ is pyridyl group substituted with at least one substituent selected from the group consisting of lower alkyl group, halogen substituted lower alkyl group, lower alkoxy group and halogen substituted lower alkoxy group, examples of lower alkyl groups include $C_1$-$C_4$ alkyl groups such as methyl, ethyl, n-propyl, isopropyl, n-butyl, isobutyl, sec-butyl, and tert-butyl. Among these, methyl and ethyl are preferable.

Examples of halogen substituted lower alkyl groups include halogen substituted $C_1$-$C_4$ alkyl groups such as fluoromethyl, difluoromethyl, trifluoromethyl, and 2,2,2-trifluoroethyl.

Examples of lower alkoxy groups include $C_1$-$C_4$ alkoxy groups such as methoxy, ethoxy, n-propoxy, isopropoxy, n-butyloxy, isobutyloxy, sec-butyloxy, and tert-butyloxy.

Examples of halogen substituted lower alkoxy groups include halogen substituted $C_1$-$C_4$ alkoxy groups such as fluoromethoxy, difluoromethoxy, trifluoromethoxy, and 2,2,2-trifluoroethoxy.

Pyridyl group has 1 to 3 (preferably, 1) substituents selected from the group consisting of the above-mentioned substituents.

Specific examples of the substituted-pyridyl groups represented by $Ar^2$ include lower alkylpyridyl groups (e.g., 3-methylpyridin-2-ly and 3-ethylpyridin-2-ly), halogen substituted lower alkylpyridyl groups (e.g., 3-fluoromethylpyridin-2-ly, 3-difluoromethylpyridin-2-ly, and 3-trifluoromethylpyridin-2-ly), lower alkoxypyridyl groups (e.g., 3-methoxypyridin-2-ly and 3-ethoxypyridin-2-ly), and halogen substituted lower alkoxypyridyl groups (e.g., 3-fluoromethoxypyridin-2-ly, 3-difluoromethoxypyridin-2-ly, and 3-trifluoromethoxypyridin-2-ly). Among these, 3-methylpyridin-2-ly is preferable.

Compound (26) can be produced by reacting compound (24) with compound (25) in a solvent and in the presence of a base, and then treating the result with an acid.

The solvent used in the reaction between compound (24) and compound (25) is not particularly limited as long as it does not adversely affect the reaction. Examples thereof include ketone solvents (e.g., acetone and methyl ethyl ketone), ether solvents (e.g., tetrahydrofuran, dioxane, diethylether, and diglyme), ester solvents (e.g., methyl acetate and ethyl acetate), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, N,N-dimethylformamide is preferable.

As the bases, known inorganic and organic bases can be used. Examples of inorganic bases include alkali metals (e.g., sodium and potassium), alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower ($C_1$-$C_3$) alkoxides (e.g., sodium methoxide and sodium ethoxide), and alkali metal hydrides (e.g., sodium hydride and potassium hydride). Examples of organic bases include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), and 1,8-diazabicyclo[5.4.0]undec-7-ene (DBU). When these bases are in a liquid form, they may also be used as a solvent. These bases may be used singly or as a mixture of two or more. Among these, alkali metal carbonates (e.g., lithium carbonate, sodium carbonate, potassium carbonate, and cesium carbonate) are preferable.

The amount of base used is generally 0.5 to 20 mol, and preferably 0.5 to 5 mol per mole of compound (25).

The proportion between compound (24) and compound (25) is generally at least 1 mol, and preferably about 1 to 5 mol of the latter per mole of the former.

The reaction temperature is not particularly limited, and the reaction may generally be conducted under cooling, at room temperature, or under heating. The reaction is preferably conducted under the temperature conditions of about 0 to 100° C. for 1 to 30 hours.

The reaction described above allows the obtaining of an addition product of the reaction between compound (24) and compound (25) represented by formula (26'):

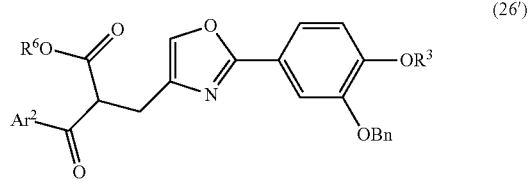

(26')

wherein $R^3$, $R^6$ and $Ar^2$ are as defined above.

Compound (26') is subsequently supplied to the reaction with an acid.

The reaction of compound (26') with an acid can be conducted in a solvent by reacting compound (26') with an acid, wherein compound (26) can be produced through hydrolyzation, decarboxylation, and debenzylation.

The solvent is not particularly limited, as long as it does not adversely affect the reaction. Examples thereof include water, alcoholic solvents (e.g., methanol, ethanol, isopropanol, and n-butanol), ketone solvents (e.g., acetone and methyl ethyl ketone), ether solvents (e.g., tetrahydrofuran, dioxane, diethylether, dimethoxyethane, and diglyme), ester solvents (e.g., methyl acetate and ethyl acetate), aromatic hydrocarbons (e.g., toluene and xylene), aprotic polar solvents (e.g., acetonitrile, N,N-dimethylformamide, and dimethylsulfoxide), halogenated hydrocarbon solvents (e.g., methylene chloride and ethylene chloride), and mixed solvents thereof. Among these, water and alcoholic solvents (e.g., methanol and ethanol) are preferable.

As the acid, known inorganic and organic acids may be used. Examples of inorganic acids include hydrohalic acids (e.g., hydrochloric acid and hydrobromic acid), sulfuric acid, nitric acid, and phosphoric acid. Examples of organic acids include formic acid, acetic acid, propionic acid, p-toluenesulfonic acid, methanesulfonic acid, and trifluoromethanesulfonic acid. When these acids are in a liquid form, they may be used as a solvent. These acids may be used singly or as a mixture of two or more. Among these, inorganic acids are preferable, and hydrohalic acids (in particular, hydrobromic acid) are particularly preferable.

The amount of acid used is generally 0.5 to 100 mol and preferably 1 to 50 mol per mole of compound (26').

The reaction temperature is not particularly limited, and the reaction may generally be conducted under cooling, at room temperature, or under heating. The reaction is preferably conducted under the temperature conditions of about 0 to 100° C. for 1 to 30 hours. Compound (26) can thus be produced.

Compound (25) is commercially available, or can be synthesized by or based on the method disclosed in a document such as Hong-yu Li et al., Tetrahedron, 2007, 63, 11763-11770.

Compound (26)+(27)→(2):

Compound (2) can be produced by reacting compound (26) with compound (27) in the presence of a base.

Examples of lower alkyl groups represented by $R^4$ include $C_1$-$C_6$ (in particular, $C_1$-$C_4$) linear or branched alkyl groups. Specific examples thereof include methyl, ethyl, n-propyl, isopropyl, n-butyl, isobutyl, sec-butyl, tert-butyl, 1-ethylpropyl, n-pentyl, neopentyl, n-hexyl, isohexyl, and 3-methylpentyl. Among these, methyl, ethyl, isopropyl, and isobutyl are preferable.

Examples of cycloalkyl lower alkyl groups represented by $R^4$ include $C_3$-$C_6$ cycloalkyl $C_1$-$C_3$ alkyl groups. Specific examples thereof include cyclopropyl methyl, 2-(cyclopropyl)ethyl, 3-(cyclopropyl)propyl, cyclobutyl methyl, 2-(cyclobutyl)ethyl, and 3-(cyclobutyl)propyl. Among these, cyclopropyl methyl and cyclobutyl methyl are preferable.

Examples of lower alkenyl groups represented by $R^4$ include $C_2$-$C_6$ (in particular, $C_2$-$C_4$) linear or branched alkenyl groups. Specific examples thereof include vinyl, allyl, and crotyl. Among these, allyl is preferable.

Examples of halogen atoms represented by $X^7$ include fluorine, chlorine, bromine, and iodine. Among these, chlorine, bromine, and iodine are preferable.

The reaction can be conducted by or based on the conditions for the reaction of compound (3)→(3') or compound (9)→(11) in Reaction Scheme 1.

In each step in Reaction Scheme 3, after completion of the reaction, the target compound can be obtained from the reaction mixture by a known isolation operation (such as filtration, concentration, or extraction). The method of the present invention does not use 1,3-dihaloacetone, which is required in the method of Patent Literature 1, and allows the target product to be produced in a simple and effective manner without using column chromatography throughout the production processes thereof.

EXAMPLES

Using Reference Examples and Examples, the present invention is explained in detail below; however, the present invention is not limited thereto.

Example 1

Compound (1a) was produced according to the following reactions.

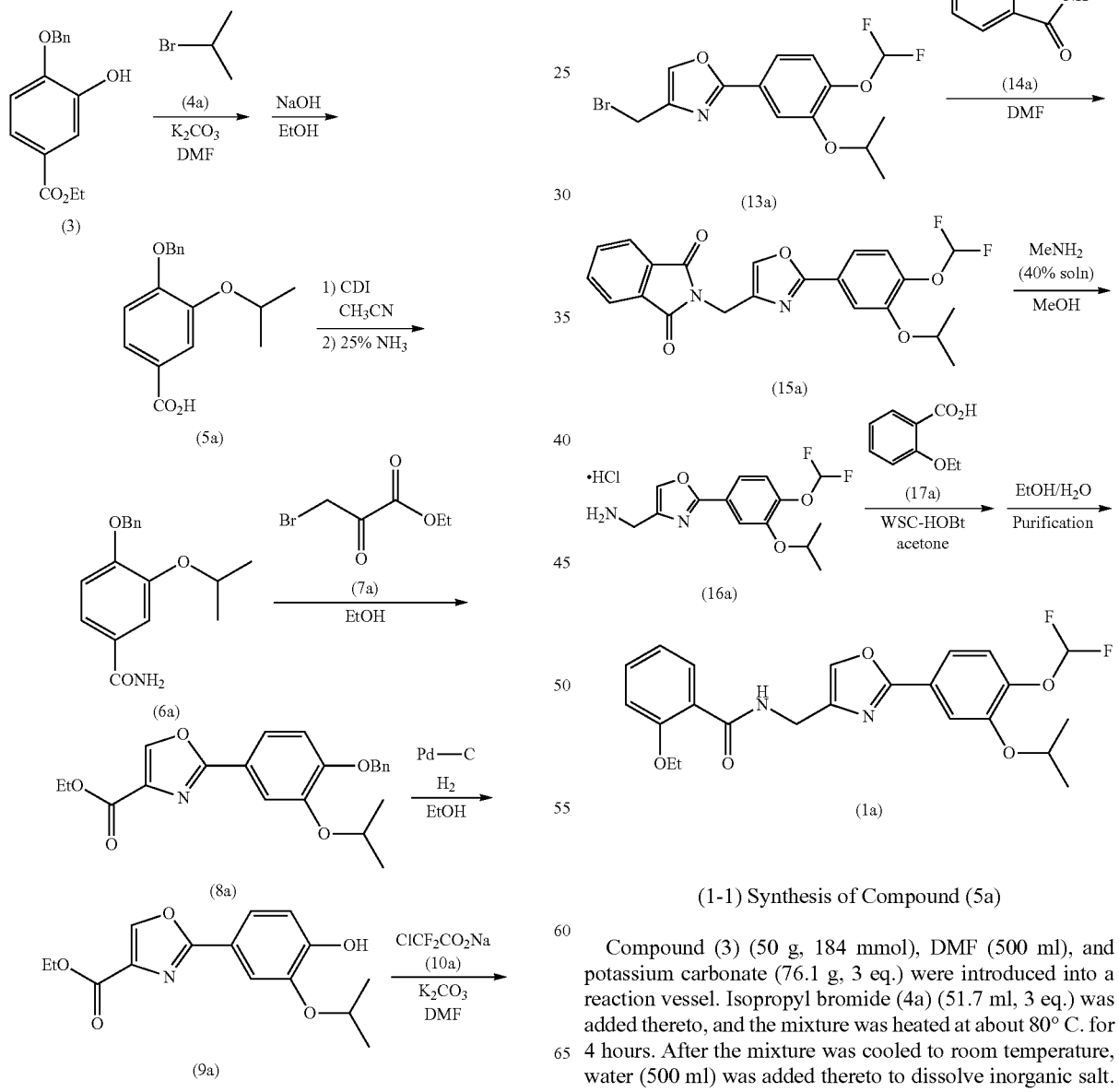

(1-1) Synthesis of Compound (5a)

Compound (3) (50 g, 184 mmol), DMF (500 ml), and potassium carbonate (76.1 g, 3 eq.) were introduced into a reaction vessel. Isopropyl bromide (4a) (51.7 ml, 3 eq.) was added thereto, and the mixture was heated at about 80° C. for 4 hours. After the mixture was cooled to room temperature, water (500 ml) was added thereto to dissolve inorganic salt. AcOEt (500 ml) was then added thereto, and extraction and liquid separation was performed. The organic layer was washed with water (500 ml) twice, and then concentrated to dryness to obtain an oily product of ethyl 4-(benzyloxy)-3-isopropoxybenzoate. EtOH (500 ml) was added to the resulting oil and dissolved. A 25% NaOH aqueous solution (50 ml) was added thereto, and the mixture was heated under stirring at 50° C. or more for about 1 hour. After the completion of the reaction, water (250 ml) and concentrated hydrochloric acid (50 ml) were added. After the reaction mixture was cooled, the precipitated crystals were collected by filtration and dried at 80° C. to give crystal Compound (5a) (48.65 g).

Compound (5a):

$^1$H NMR (CDCl$_3$, 300 MHz) δ 1.39 (d, J=6.0 Hz, 6H), 4.61 (sept, J=6.0 Hz, 1H), 5.21 (s, 2H), 6.94 (d, J=8.4 Hz, 1H), 7.29-7.45 (m, 5H), 7.65 (d, J=2.1 Hz, 2H), 7.69 (dd, J=8.4 Hz, 2.1 Hz, 2H).

(1-2) Synthesis of Compound (6a)

Compound (5a) (48 g, 168 mmol) was added to acetonitrile (480 ml), and then CDI (1,1'-carbonyldiimidazole) (32.6 g, 1.2 eq.) was added thereto. The mixture was then stirred at 55° C. for 1 hour to obtain an active ester solution. The solution was added to the mixed solution of water (432 ml) and 25% aqueous ammonia (48 ml). The mixture was stirred, and the precipitated crystals were collected by filtration and dried at 60° C. to give Compound (6a) (45.83 g).

Compound (6a):

$^1$H NMR (CDCl$_3$, 300 MHz) δ 1.38 (d, J=6.3 Hz, 6H), 4.62 (sept, J=6.3 Hz, 1H), 5.19 (s, 2H), 6.91 (d, J=8.4 Hz, 1H), 7.27-7.49 (m, 7H).

(1-3) Synthesis of Compound (8a)

Compound (6a) (20 g, 70.1 mmol) was added to EtOH (300 ml), ethyl bromopyruvate (7a) (26.5 ml, 3 eq.) was added thereto, and the mixture was heated at reflux for 5 hours. After the completion of the reaction, water (150 ml) was added thereto, and cooled. The precipitated crystals were collected by filtration and dried at 60° C. to give Compound (8a) (15.96 g).

Compound (8a):

$^1$H NMR (CDCl$_3$, 300 MHz) δ 1.39 (d, J=6.3 Hz, 6H), 1.41 (t, J=6.9 Hz, 3H), 4.43 (sept, J=6.3 Hz, 1H), 5.19 (s, 2H), 6.97 (d, J=8.4 Hz, 1H), 7.28-7.46 (m, 5H), 7.64 (dd, J=8.4 Hz, 1.8 Hz, 1H), 7.69 (d, J=1.8 Hz, 1H), 8.22 (s, 1H).

(1-4) Synthesis of Compound (9a)

Compound (8a) (32 g, 83.9 mmol) and EtOH (640 mL) were added to a pressurized vessel. A 5% Pd—C (wet) (6.9 g) was added thereto and cooled at about 10° C., and H$_2$ gas (theoretical amount: 1 eq.) was absorbed. After the absorption, the mixture was heated to around room temperature. After the catalyst was removed by filtration, the filtrate was concentrated to about 90 ml, and water (96 ml) was added to the concentrated reaction mixture. The precipitated crystals were collected by filtration, and dried at 60° C. to give Compound (9a) (22.9 g).

Compound (9a):

$^1$H NMR (CDCl$_3$, 300 MHz) δ 1.40 (d, J=6.0 Hz, 6H), 1.41 (t, J=7.2 Hz, 3H), 4.43 (q, J=7.2 Hz, 2H), 4.43 (sept, J=6.0 Hz, 1H), 6.04 (s, 1H), 6.99 (d, J=8.4 Hz, 1H), 7.61 (dd, J=8.4 Hz, 1.8 Hz, 1H), 7.65 (d, J=1.8 Hz, 1H), 8.21 (s, 1H).

(1-5) Synthesis of Compound (11a)

After Compound (9a) (40 g, 137 mmol) and sodium chlorodifluoroacetate (10a) (25.1 g, 1.2 eq.) were dissolved in DMF (400 ml), potassium carbonate (22.8 g, 1.2 eq.) was added thereto and heated under stirring at about 80° C. for 1 hour. After the mixture was cooled to around room temperature, water (600 ml) and AcOEt (600 ml) were added thereto, and extraction and liquid separation was performed. After the organic layer was washed with a 5% NaCl aqueous solution (400 ml), it was concentrated to dryness to obtain an oily product of Compound (11a). The resulting oily product was dissolved in EtOH (200 ml), and concentrated hydrochloric acid (20 ml) was added thereto. The mixture was heated at reflux for 30 minutes. After the completion of the reaction, EtOH was distilled off. CPME (cyclopentyl methyl ether) (400 ml) was added to the residue oil and dissolved, and then washed with a 1N—NaOH aqueous solution (240 ml) twice. After the organic layer was further washed with water (400 ml) twice, it was concentrated to dryness to give solid Compound (11a) (24.4 g).

Compound (11a):

$^1$H NMR (CDCl$_3$, 300 MHz) δ 1.40 (d, J=6.0 Hz, 6H), 1.42 (t, J=7.2 Hz, 3H), 4.44 (q, J=7.2 Hz, 2H), 4.72 (sept, J=6.0 Hz, 1H), 6.64 (t, J=75 Hz, 1H), 7.24 (d, J=8.1 Hz, 1H), 7.66 (dd, J=8.1 Hz, 1.8 Hz, 1H), 7.75 (d, J=1.8 Hz, 1H), 8.26 (s, 1H).

(1-6) Synthesis of Compound (12a)

Compound (11a) (0.5 g, 1.46 mmol) and zinc chloride (0.2 g, 1 eq.) were added to DME (2.5 ml) and cooled. NaBH$_4$ (0.11 g, 2 eq.) was added thereto, and the mixture was heated at reflux and reacted for 1 hour. The reaction mixture was cooled, and added to a mixed solution of water (5 ml) and concentrated hydrochloric acid (0.75 ml). The mixture was then cooled and stirred. The precipitated crystals were collected by filtration and dried at 60° C. to give Compound (12a) (0.37 g).

Compound (12a):

$^1$H NMR (CDCl$_3$, 300 MHz) δ 1.40 (d, J=5.7 Hz, 6H), 2.33 (br-s, 1H), 4.64-4.77 (m, 3H), 6.63 (t, J=75 Hz, 1H), 7.23 (d, J=8.4 Hz, 1H), 7.59 (dd, J=8.4 Hz, 1.8 Hz, 1H), 7.65 (s, 1H), 7.67 (d, J=1.8 Hz, 1H).

(1-7) Synthesis of Compound (13a)

Compound (12a) (13 g, 43.4 mmol) was added to AcOEt (260 ml), followed by dissolution by heating. After the mixture was cooled, triethylamine (12.1 ml, 2 eq.) was added thereto, and stirred. Methanesulfonyl chloride (5.0 ml, 1.5 eq.) was added dropwise to the solution, and stirred at room temperature for 1 hour. Subsequently, LiBr (11.3 g, 3 eq.) was added, and reacted at 30° C. for 1 hour (bromination). After the completion of the reaction, water (260 ml) was added, and extraction was performed. The organic layer was concentrated to dryness to give solid Compound (13a) (15.13 g).

Compound (13a):

$^1$H NMR (CDCl$_3$, 300 MHz) δ 1.41 (d, J=6.0 Hz, 6H), 4.44 (s, 2H), 4.71 (sept, J=6.0 Hz, 1H), 6.63 (t, J=75 Hz, 1H), 7.23 (d, J=8.1 Hz, 1H), 7.60 (dd, J=8.1 Hz, 2.4 Hz, 1H), 7.70 (s, 1H).

(1-8) Synthesis of Compound (15a)

Compound (13a) (20 g, 55.2 mmol) was dissolved in DMF (200 ml), potassium phthalimide (15.34 g, 1.5 eq.) was added thereto, and the mixture was heated under stirring at 80° C. for 1 hour. After the mixture was cooled to around room temperature, water (200 ml) was added thereto, then the precipitated crystals were collected by filtration and dried at 80° C. to give Compound (15a) (20.57 g).

Compound (15a):

$^1$H NMR (CDCl$_3$, 300 MHz) δ 1.38 (d, J=6.3 Hz, 6H), 4.68 (sept, J=6.3 Hz, 1H), 6.60 (t, J=75 Hz, 1H), 7.18 (d, J=8.4 Hz, 1H), 7.56 (dd, J=8.4 Hz, 1.8 Hz, 1H), 7.61 (d, J=1.8 Hz, 1H), 7.71-7.72 (m, 2H), 7.85-7.90 (m, 2H).

(1-9) Synthesis of Compound (16a)

Compound (15a) (10 g, 23 mmol) and a 40% methyl amine aqueous solution (20 ml) were added to MeOH (80 ml), and the mixture was heated at reflux for 30 minutes. After the completion of the reaction, MeOH was distilled off, and 1N—NaOH aqueous solution (120 ml) and AcOEt (100 ml) were added to perform extraction. The organic layer was washed with a 5% NaCl aqueous solution (120 ml) twice, and then concentrated to dryness. After CPME (150 ml) was added to the residue and dissolved, a 4N—HCl/CPME solution (6 ml, 1.04 eq.) was added dropwise. After the reaction mixture was cooled, the precipitated crystals were collected by filtration, and dried at 60° C. to give Compound (16a) (6.39 g).

Compound (16a):

$^1$H NMR (CDCl$_3$, 300 MHz) δ 1.37 (d, J=6.3 Hz, 6H), 4.24 (br-s, 2H), 4.64 (sept, J=6.3 Hz, 1H), 6.59 (t, J=75 Hz, 1H), 7.16 (d, J=8.7 Hz, 1H), 7.48 (d, J=8.7 Hz, 1H), 7.56 (s, 1H), 7.90 (s, 1H), 8.84 (br-s, 2H).

(1-10) Synthesis of Compound (1a)

Compound (16a) (20 g, 59.7 mmol) was added to AcOEt (400 ml), and then 5% sodium bicarbonate water (200 ml) was added thereto. The mixture was stirred at 50° C. for about 10 minutes. After liquid separation, the organic layer was washed with a 5% NaCl aqueous solution (200 ml), and concentrated to dryness. Acetone (400 ml), 2-ethoxy benzoic acid (10.4 g, 1.05 eq.), WSC (12.6 g, 1.1 eq.), and HOBt (8.88 g, 1.1 eq.) were added to the residue, and the mixture was heated at reflux for 1 hour. After the completion of the reaction, a 25% NaOH aqueous solution (40 ml) was added and heated at reflux for another 10 minutes. Subsequently, acetone (200 ml) was distilled off from the reaction mixture, and water (200 ml) and AcOEt (200 ml) were added to perform extraction. After the organic layer was washed with a 1N—HCl aqueous solution (220 ml), 5% NaCl aqueous solution (200 ml), and water (60 ml), it was concentrated to dryness to obtain an oily product. EtOH (100 ml) and water (40 ml) were added and dissolved in the oily product, and a seed crystal was added thereto, followed by cooling and aging. The precipitated crystals were then collected by filtration and dried at 35 to 40° C. to give Compound (1a) (18.58 g).

Compound (1a):

$^1$H NMR (CDCl$_3$, 300 MHz) δ 1.40 (d, J=6.3 Hz, 6H), 1.49 (t, J=6.9 Hz, 3H), 4.19 (q, J=6.9 Hz, 2H), 4.62-4.74 (m, 3H), 6.63 (t, J=75 Hz, 1H), 6.95 (d, J=8.4 Hz, 1H), 7.08 (t, J=7.5 Hz, 1H), 7.21-7.26 (m, 1H), 7.40-7.46 (m, 1H), 7.57-7.65 (m, 2H), 7.67 (1H, s), 8.24 (dd, J=7.5, 1.8 Hz, 1H), 8.57 (br-s, 1H).

Example 2

Compound (1b) was produced according to the following reactions.

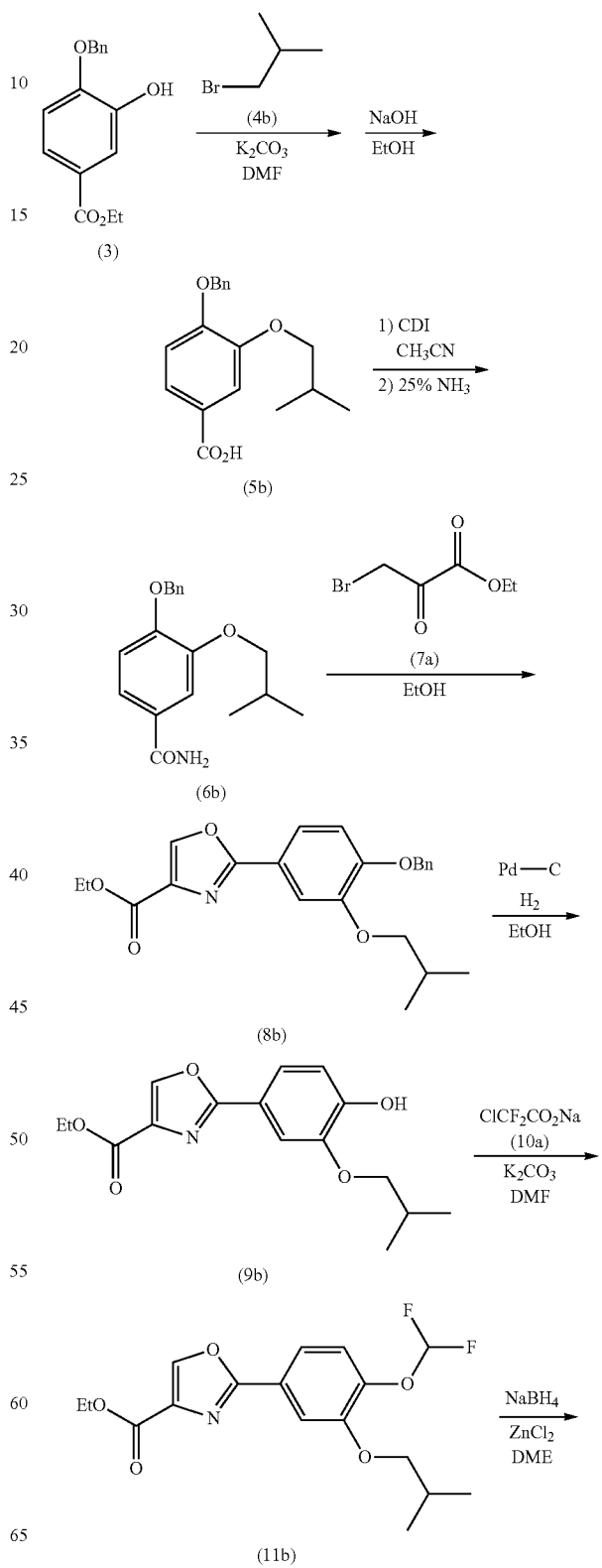

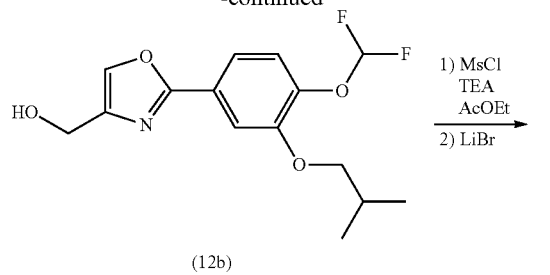

(12b)

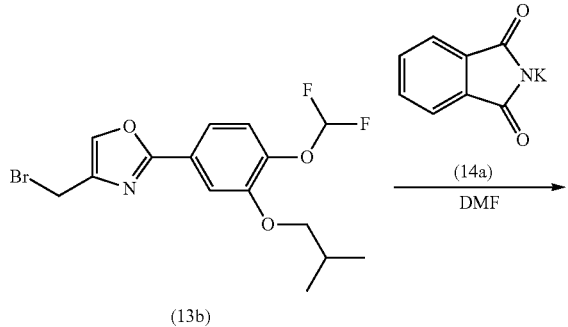

(13b)

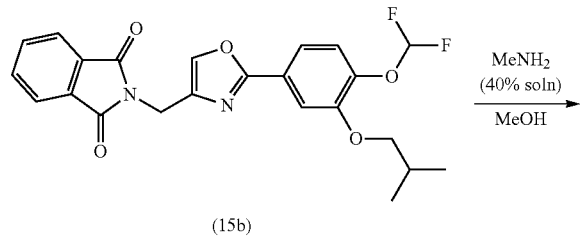

(15b)

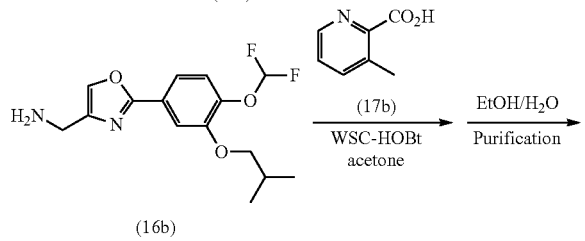

(16b)

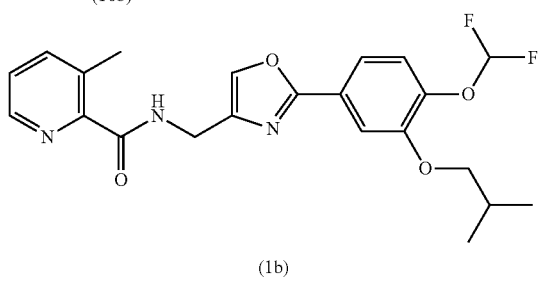

(1b)

(2-1) Synthesis of Compound (5b)

Compound (3) (5.3 g), ethanol (75 ml), and DBU (8.9 g) were introduced into a reaction vessel, and isobutyl bromide (4b) (8 ml, 3 eq.) was added thereto. The mixture was heated at reflux overnight. After the mixture was cooled to room temperature, the mixture was concentrated by distilling off ethanol in vacuo. AcOEt (50 ml) was added thereto, and extraction and liquid separation was performed. After the organic layer was washed with water (50 ml) twice, it was concentrated to dryness to give a solid of ethyl 4-(benzyloxy)-3-isobutoxybenzoate. Acetonitrile (50 ml) was added to the resulting solid, followed by dissolution, and a 10% NaOH aqueous solution (28 ml) was added thereto. The resulting mixture was heated under stirring at 40° C. or more overnight. After the completion of the reaction, concentrated hydrochloric acid was added. After the reaction mixture was cooled, the precipitated crystals were collected by filtration, and dried at 80° C. to give white crystal Compound (5b) (4.67 g).

Compound (5b):
$^1$H NMR (CDCl$_3$, 300 MHz) δ 1.07 (d, J=6.9 Hz, 6H), 2.18 (sept, J=6.9 Hz, 1H), 3.85 (d, J=6.9 Hz, 2H), 5.22 (s, 2H), 6.94 (d, J=8.4 Hz, 1H), 7.29-7.47 (m, 5H), 7.60 (d, J=1.8 Hz, 1H), 7.69 (dd, J=8.4 Hz, 1.8 Hz, 1H).

(2-2) Synthesis of Compound (1b)

Compound (1b) was obtained in the same manner as or according to steps (1-2) to (1-10) in Example 1, except that Compound (5b) was used in place of Compound (5a). The $^1$H NMR data of the compound produced in each step is shown below.

Compound (6b):
$^1$H NMR (CDCl$_3$, 300 MHz) δ 1.06 (d, J=6.6 Hz, 6H), 2.16 (sept, J=6.6 Hz, 1H), 3.85 (d, J=6.6 Hz, 2H), 5.19 (s, 2H), 6.91 (d, J=8.7 Hz, 1H), 7.22-7.47 (m, 7H).

Compound (8b):
$^1$H NMR (CDCl$_3$, 300 MHz) δ 1.07 (d, J=6.6 Hz, 6H), 1.41 (t, J=7.2 Hz, 3H), 2.19 (sept, J=6.6 Hz, 1H), 3.88 (d, J=6.6 Hz, 2H), 4.43 (q, J=7.2 Hz, 2H), 5.19 (s, 2H), 6.97 (d, J=8.4 Hz, 1H), 7.28-7.47 (m, 5H), 7.60 (dd, J=8.4 Hz, 1.8 Hz, 1H), 7.66 (d, J=1.8 Hz, 1H), 8.22 (s, 1H).

Compound (9b):
$^1$H NMR (CDCl$_3$, 400 MHz) δ 1.06 (d, J=6.8 Hz, 6H), 1.41 (t, J=6.8 Hz, 3H), 2.15 (sept, J=6.8 Hz, 1H), 3.91 (d, J=6.8 Hz, 2H), 4.43 (q, J=6.8 Hz, 2H), 5.96 (s, 1H), 6.99 (d, J=8.0 Hz, 1H), 7.61 (dd, J=8.0 Hz, 2.0 Hz, 1H), 7.64 (d, J=2.0 Hz, 1H), 8.21 (s, 1H).

Compound (11b):
$^1$H NMR (CDCl$_3$, 400 MHz) δ 1.07 (d, J=6.4 Hz, 6H), 1.42 (t, J=7.2 Hz, 3H), 2.15 (sept, J=6.4 Hz, 1H), 3.88 (d, J=6.4 Hz, 2H), 4.45 (q, J=7.2 Hz, 2H), 6.63 (t, J=74.8 Hz, 1H), 7.24 (d, J=8.4 Hz, 1H), 7.64 (dd, J=8.4 Hz, 2.0 Hz, 1H), 7.73 (d, J=2.0 Hz, 1H), 8.27 (s, 1H).

Compound (12b):
$^1$H NMR (CDCl$_3$, 400 MHz) δ 1.06 (d, J=6.8 Hz, 6H), 2.17 (sept, J=6.8 Hz, 1H), 2.54 (t, J=7.0 Hz, 1H), 3.88 (d, J=6.8 Hz, 2H), 4.69 (d, J=7.0 Hz, 2H), 6.62 (t, J=75.2 Hz, 1H), 7.23 (d, J=8.8 Hz, 1H), 7.58 (dd, J=8.4 Hz, 1.6 Hz, 1H), 7.64 (d, J=1.6 Hz, 1H), 7.65 (s, 1H).

Compound (13b):
$^1$H NMR (CDCl$_3$, 400 MHz) δ 1.07 (d, J=6.8 Hz, 6H), 2.17 (sept, J=6.8 Hz, 1H), 3.88 (d, J=6.8 Hz, 2H), 4.44 (s, 2H), 6.62 (t, J=75.2 Hz, 1H), 7.23 (d, J=8.0 Hz, 1H), 7.59 (dd, J=8.4 Hz, 2.0 Hz, 1H), 7.63 (d, J=2.0 Hz, 1H), 7.71 (s, 1H).

Compound (15b):
$^1$H NMR (CDCl$_3$, 300 MHz) δ 1.06 (d, J=6.3 Hz, 6H), 2.15 (sept, J=6.3 Hz, 1H), 3.86 (d, J=6.3 Hz, 2H), 4.87 (s, 2H), 6.59 (t, J=75 Hz, 1H), 7.19 (d, J=8.4 Hz, 1H), 7.26-7.61 (m, 2H), 7.68 (s, 1H), 7.72-7.91 (m, 4H).

Compound (16b):
$^1$H NMR (CDCl$_3$, 300 MHz) δ 1.05 (d, J=6.6 Hz, 6H), 2.17 (sept, J=6.6 Hz, 1H), 3.85 (d, J=6.3 Hz, 2H), 3.89 (s, 2H), 6.62 (t, J=75 Hz, 1H), 7.23 (d, J=8.1 Hz, 1H), 7.56 (s, 1H), 7.58 (d, J=8.1 Hz, 1H), 7.63 (s, 1H).

Compound (1b):
$^1$H NMR (CDCl$_3$, 300 MHz) δ 1.06 (d, J=6.3 Hz, 6H), 2.11 (sept, J=6.3 Hz, 1H), 2.76 (s, 3H), 3.88 (d, J=6.3 Hz, 2H), 4.60 (d, J=6.0 Hz, 2H), 6.61 (t, J=75 Hz, 1H), 7.20-7.33 (m, 2H), 7.57-7.62 (m, 3H), 7.68 (s, 1H), 8.39 (br-s, 1H), 8.60 (br-s, 1H).

Examples 3 to 6

Using corresponding appropriate starting material compounds, Compounds (1c) to (1f) were synthesized in Examples 3 to 6 according to the production methods described in Examples 1 and 2 (Table 1).

processes thereof, it is preferable from the viewpoint of the health and/or safety of the people who are involved in its production. Furthermore, since this method allows purification without using column chromatography throughout the production process, it is an effective method on an industrial scale.

TABLE 1

| Example | Compound | Structural formula | $^1$H NMR (CDCl$_3$, 300 MHz) |
|---|---|---|---|
| 3 | (1c) | | 1.42 (d, J = 6.3 Hz, 6H), 1.49 (t, J = 6.9 Hz, 3H), 3.91 (s, 3H), 4.18 (q, J = 6.9 Hz, 2H), 4.59-4.72 (m, 3H), 6.91-6.96 (m, 2H), 7.07 (t, J = 7.8 Hz, 1H), 7.38-7.45 (m, 1H), 7.55-7.62 (m, 3H), 8.24 (dd, J = 7.8 Hz, 1.8 Hz, 1H), 8.57 (br-s, 1H) |
| 4 | (1d) | | 1.39 (d, J = 6.0 Hz, 6H), 2.76 (s, 3H), 4.59 (d, J = 6.0 Hz, 2H), 4.67-4.74 (m, 1H), 6.62 (t, J = 75 Hz, 1H), 7.19-7.33 (m, 2H), 7.57-7.67 (m, 4H), 8.38-8.39 (m, 1H), 8.58 (br-s, 1H) |
| 5 | (1e) | | 1.39 (d, J = 6.0 Hz, 6H), 3.91 (s, 3H), 4.61-4.70 (m, 5H), 6.61 (t, J = 75 Hz, 1H), 6.94 (d, J = 8.1 Hz, 1H), 7.15 (d, J = 8.4 Hz, 1H), 7.30-7.64 (m, 6H), 8.10 (d, J = 7.8 Hz, 1H) |
| 6 | (1f) | | 1.41 (d, J = 6.3 Hz, 6H), 2.76 (s, 3H), 3.89 (s, 3H), 4.59 (d, J = 5.7 Hz, 2H), 4.68 (sept., J = 6.3 Hz, 1H), 6.93 (d, J = 8.4 Hz, 1H), 7.28-7.33 (m, 1H), 7.57-7.63 (m, 4H), 8.39 (dd, J = 4.8 Hz, 1.2 Hz, 1H), 8.58 (br-s, 1H) |

Using known Compound (28a):

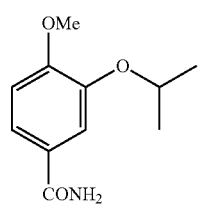

(28a)

as a starting material, Compounds (1c), (1e), and (1f) can be obtained in the same manner as or according to steps (1-3) and (1-6) to (1-10) of Example 1.

Since the production method of the present invention does not use a dihaloketone compound, which is harmful to humans, or explosive hydrazine throughout the production

Example 7

Compound (2a) was produced according to the following reactions.

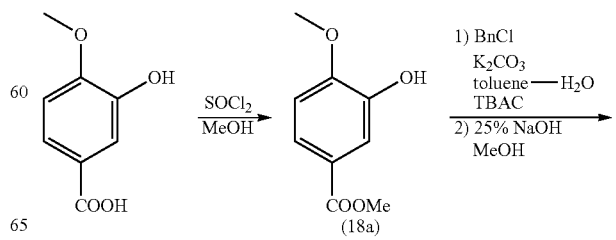

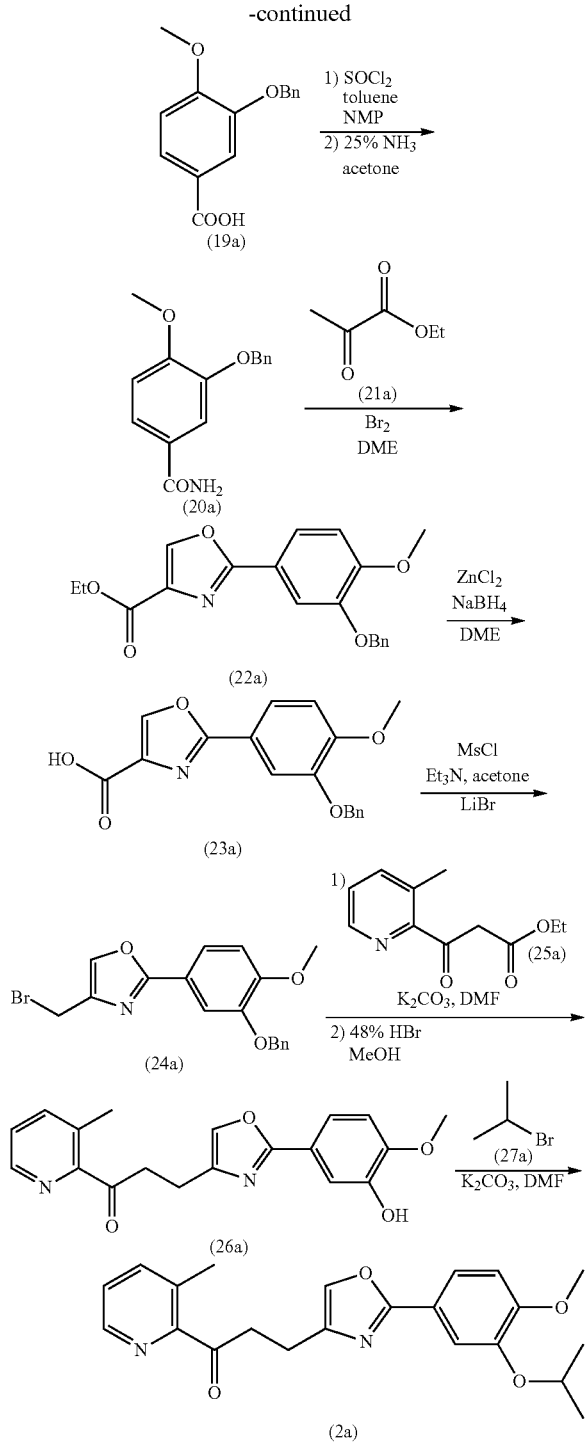

(7-1) Synthesis of Compound (18a)

Isovanillic acid (50 g, 0.3 mol), MeOH (500 ml), and thionyl chloride (23.6 ml) were introduced into a reaction vessel, and the mixture was heated at reflux for 2 hours. After cooling, the mixture was neutralized with a 25% NaOH aqueous solution, and water (250 ml) and activated carbon (2.5 g) were added thereto. After the mixture was stirred at room temperature, insoluble matter was filtrated. The filtrate was concentrated and extracted with AcOEt (350 ml). After the organic layer was separated, it was concentrated by distilling off the solvent to give oily Compound (18a) (54 g).

Compound (18a):
$^1$H NMR (CDCl$_3$, 300 MHz) δ 3.90 (s, 3H), 3.98 (s, 3H), 5.63 (s, 1H), 6.67 (d, J=8.1 Hz, 1H), 7.58-7.63 (m, 2H).

(7-2) Synthesis of Compound (19a)

Compound (18a) (2 g, 11 mmol), toluene (10 ml), benzyl chloride (1.8 g, 1.3 eq.), and TBAC (0.31 g, 0.1 eq.) were introduced into a reaction vessel, and the mixture was heated at 80° C. for 2 hours. The mixture was cooled to 50° C., and the organic layer was separated by liquid separation. Thereafter, MeOH (4 ml) and a 25% NaOH aqueous solution (4 ml) were added thereto, followed by heating at reflux for 2 hours. After cooling, hydrochloric acid (3 ml) was added and stirred, and then the precipitated crystals were collected by filtration and dried at 60° C. to give crystal Compound (19a) (2.55 g).

Compound (19a):
$^1$H NMR (CDCl$_3$, 300 MHz) δ 3.95 (s, 3H), 5.19 (s, 2H), 6.94 (d, J=8.4 Hz, 1H), 7.29-7.48 (m, 5H), 7.65 (d, J=1.8 Hz, 1H), 7.77 (dd, J=8.4 Hz, 1.8 Hz, 1H).

(7-3) Synthesis of Compound (20a)

Compound (19a) (78.5 g, 0.3 mol), toluene (400 ml), thionyl chloride (39.8 g, 1.1 eq.), and NMP (7.9 ml, 0.1 eq.) were introduced, and the mixture was stirred at room temperature for 2 hours. The resulting acid chloride solution was added dropwise to a mixture of 25% aqueous ammonia (157 ml) and water (235.5 ml) while stirring under ice-cooling. Acetone (157 ml) was added to the reaction mixture, and the mixture was stirred at 50° C. for 30 minutes, and cooled to room temperature. The precipitated crystals were collected by filtration, and dried at 60° C. to give crystal Compound (20a) (68.6 g).

Compound (20a):
$^1$H NMR (CDCl$_3$, 300 MHz) δ 3.93 (s, 3H), 5.18 (s, 2H), 5.67 (br-s, 2H), 6.90 (d, J=1.8 Hz, 1H), 7.28-7.85 (m, 7H).

(7-4) Synthesis of Compound (22a)

Ethyl pyruvate (21a) (10 g) and DME (100 ml) were introduced into a reaction vessel, and bromine (4 ml) was added dropwise. The mixture was heated under stirring at 60° C. for 1 hour. Compound (20a) (8.9 g) synthesized in Step (7-3) was added thereto, and the mixture was heated at reflux for 8 hours. After the completion of the reaction, water (100 ml) was added thereto to cool the mixture. The precipitated crystals were then collected by filtration and dried at 60° C. to give crystal Compound (22a) (6.92 g).

Compound (22a):
$^1$H NMR (CDCl$_3$, 500 MHz) δ 1.41 (d, J=7.5 Hz, 3H), 3.93 (s, 3H), 4.43 (q, J=7.5 Hz, 2H), 6.96 (d, J=9.0 Hz, 1H), 7.30-7.49 (m, 2H), 7.71 (d, J=2.0 Hz, 1H), 8.22 (s, 1H).

Compound (22a) can also be produced by reacting compound (20a) and ethyl bromopyruvate (7a) according to Step (1-3) of Example 1.

(7-5) Synthesis of Compound (23a)

Compound (22a) (6.92 g, 20 mmol), DME (70 ml), zinc chloride (2.67 g, 1 eq.), and NaBH$_4$ (1.48 g, 2 eq.) were introduced into a reaction vessel, and heated under stirring at 50° C. for 5 hours. After cooling, water (70 ml) and hydrochloric acid (3.5 ml) were added and stirred, and the precipitated crystals were collected by filtration and dried at 60° C. to give Compound (23a) (6.1 g).
Compound (23a):
  $^1$H NMR (CDCl$_3$, 300 MHz) δ 2.72 (d, J=4.8 Hz, 1H), 3.92 (s, 3H), 4.66 (d, J=4.8 Hz, 2H), 5.20 (s, 2H), 6.95 (d, J=9.0 Hz, 1H), 7.28-7.67 (m, 8H).

(7-6) Synthesis of Compound (24a)

Compound (23a) (8.8 g), acetone (88 ml), and triethylamine (4.3 g) were introduced into a reaction vessel, and MsCl (3.89 g) was added dropwise while stirring under ice-cooling. After completion of the dropwise addition, the mixture was further stirred for 1 hour. Lithium bromide (12.3 g) was then added to the mixture, and stirred for 2 hours. After the completion of the reaction, water (88 ml) was added thereto, and the precipitated crystals were collected by filtration and dried at 60° C. to give Compound (24a) (9.5 g).
Compound (24a):
  $^1$H NMR (CDCl$_3$, 500 MHz) δ 3.93 (s, 3H), 4.43 (s, 2H), 5.21 (s, 2H), 6.95 (d, J=8.5 Hz, 1H), 7.30-7.49 (m, 2H), 7.62 (d, J=2.0 Hz, 1H), 7.65 (s, 1H).

(7-7) Synthesis of Compound (26a)

Compound (24a) (9.25 g) and Compound (25a) (a commercially available product or a product obtained according to the method described in "Tetrahedron, 2007, 63, 11763-11770" written by Hong-yu Li et al.) (15.4 g) were dissolved in DMF (92 ml). K$_2$CO$_3$ (5.1 g) was added thereto while stirring under ice-cooling, and the mixture was stirred for 2 hours. After the completion of the reaction, water (46 ml) and ethyl acetate (93 ml) were added to perform extraction. After the organic layer was washed with aqueous sodium bicarbonate solution, MeOH (18.5 ml) and 48% hydrobromic acid (74 ml) were added thereto, and the mixture was heated at reflux for 2 hours. After the completion of the reaction, water and ethyl acetate were added to perform extraction. The organic layer was then washed with aqueous sodium bicarbonate solution, then organic layer was separated, and concentrated to dryness. The crude product was re-crystallized from 50% water-containing ethanol (93 ml), and the obtained crystals were dried at 50° C. to give Compound (26a) (4.74 g).
Compound (26a):
  $^1$H NMR (CDCl$_3$, 300 MHz) δ 2.57 (s, 3H), 3.00 (t, J=7.5 Hz, 2H), 3.58 (t, J=7.5 Hz, 2H), 3.93 (s, 3H), 5.68 (s, 1H), 6.89 (dd, J=7.8 Hz, 1.2 Hz, 1H), 7.29-7.41 (m, 1H), 7.44 (d, J=0.9 Hz, 1H), 7.51-7.60 (m, 3H), 8.49 (dd, J=4.5 Hz, 1.2 Hz, 1H).

(7-8) Synthesis of Compound (2a)

Compound (26a) (2.95 g), potassium carbonate (3.6 g), and isopropyl bromide (27a) (3.2 g) were added to DMF (30 ml), and heated under stirring at 60° C. for 3 hours. After the reaction mixture was cooled, water (30 ml) was added thereto to further cool the mixture. The precipitated crystals were collected by filtration and dried at 50° C. to give Compound (2a) (3.17 g).
Compound (2a):
  $^1$H NMR (CDCl$_3$, 300 MHz) δ 1.39 (d, J=6.0 Hz, 6H), 2.62 (s, 3H), 3.00 (t, J=7.5 Hz, 2H), 3.59 (t, J=7.5 Hz, 2H), 3.89 (s, 3H), 4.65 (tt, J=6.0 Hz, 1H), 6.91 (d, J=8.7 Hz, 1H), 7.31-7.34 (m, 1H), 7.45 (s, 1H), 7.53-7.59 (m, 3H), 8.50 (dd, J=4.5 Hz, 1.2 Hz, 1H).

Example 8

Compound (2b) was produced according to the following reactions.

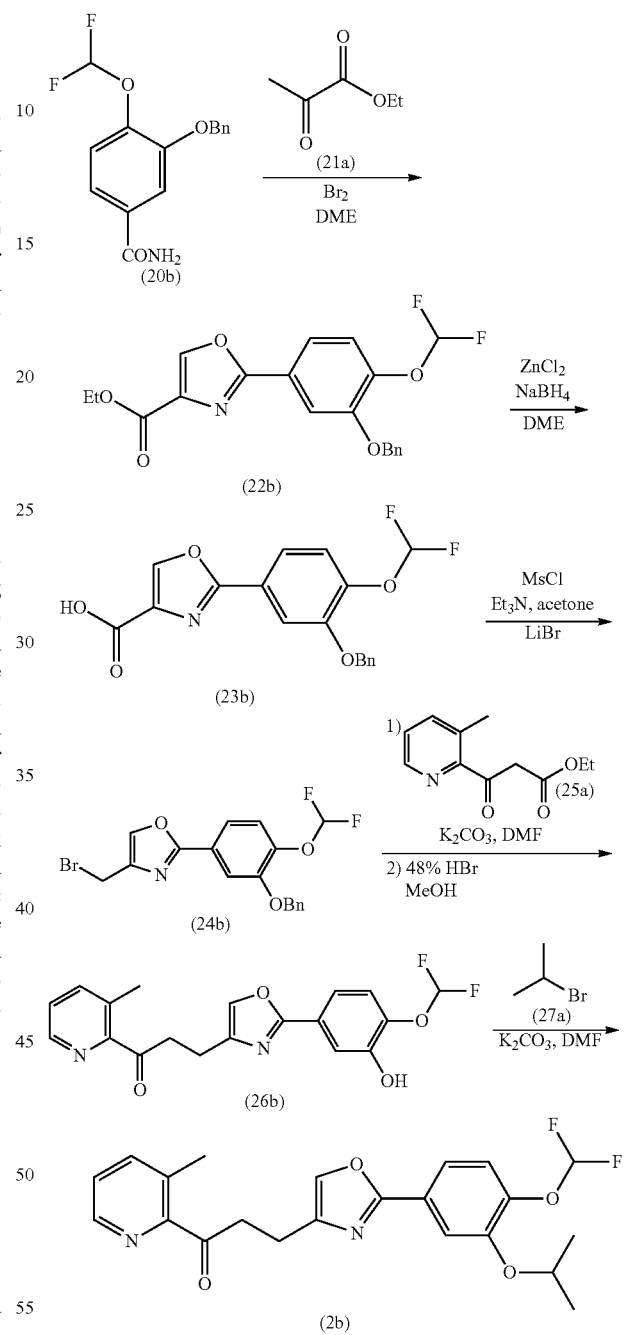

Compound (2b) was obtained by performing the treatment in the same manner as or according to Steps (7-4) to (7-8) of Example 7, except that known Compound (20b) was used in place of Compound (20a). The $^1$H NMR data of the compound produced in each step is shown below.
Compound (22b):
  $^1$H-NMR (CDCl$_3$, 300 MHz) δ 1.42 (t, J=7.2 Hz, 3H), 4.44 (q, J=7.2 Hz, 2H), 5.22 (s, 2H), 6.64 (t, J=74.7 Hz, 1H), 7.24-7.48 (m, 6H), 7.70 (dd, J=8.4 Hz, 2.1 Hz, 1H), 7.85 (d, J=2.1 Hz, 1H), 8.27 (s, 1H).

According to Step (1-3) of Example 1, Compound (22b) can be produced by reacting Compound (20b) with ethyl bromopyruvate (7a).

Compound (23b):
¹H-NMR (CDCl₃, 300 MHz) δ 2.06 (br-s, 1H), 4.69 (br-s, 2H), 5.22 (s, 2H), 7.25-7.48 (m, 6H), 7.60-7.66 (m, 2H), 7.75 (s, 1H).

Compound (24b):
¹H-NMR (CDCl₃, 300 MHz) δ 4.45 (s, 2H), 5.22 (s, 2H), 6.63 (t, J=74.7 Hz, 1H), 7.25-7.49 (m, 6H), 7.64 (dd, J=8.4 Hz, 1.8 Hz, 1H), 7.72 (s, 1H), 7.76 (d, J=1.8 Hz, 1H).

Compound (26b):
¹H-NMR (CDCl₃, 300 MHz) δ 2.57 (s, 3H), 3.01 (t, J=7.5 Hz, 2H), 3.60 (t, J=7.5 Hz, 2H), 5.76 (s, 1H), 6.58 (t, J=75 Hz, 1H), 7.16 (d, J=8.1 Hz, 1H), 7.30-7.33 (m, 1H), 7.45-7.67 (m, 4H), 8.50 (dd, J=4.5 Hz, 1.2 Hz, 1H).

Compound (2b):
¹H-NMR (CDCl₃, 300 MHz) δ 1.39 (d, J=6.0 Hz, 6H), 2.58 (s, 3H), 3.02 (t, J=7.2 Hz, 2H), 3.61 (t, J=7.2 Hz, 2H), 4.69 (sept, J=6.0 Hz, 1H), 6.61 (t, J=75 Hz, 1H), 7.20 (d, J=8.1 Hz, 1H), 7.31-7.35 (m, 1H), 7.50 (s, 1H), 7.53-7.63 (m, 3H), 8.51 (dd, J=4.8 Hz, 0.9 Hz, 1H).

Examples 9 to 17

According to the production methods of Examples 7 and 8, Compounds (2c) to (2k) were synthesized in Examples 9 to 17 using an appropriate starting material compound (Table 2).

TABLE 2

| Example | Compound | Structural formula | ¹H NMR (CDCl₃, 300 MHz) |
|---|---|---|---|
| 9 | (2c) | | 0.36-0.40 (m, 2H), 0.64-0.67 (m, 2H), 1.47 (m, 1H), 1.51 (t, J = 7.2 Hz, 3H), 2.99 (t, J = 6.6 Hz, 2H), 3.41 (t, J = 6.6 Hz, 2H), 3.91-3.93 (m, 5H), 4.13 (q, J = 7.2 Hz, 2H), 6.89-7.00 (m, 3H), 7.39-7.45 (m, 2H), 7.50 (s, 1H), 7.56 (dd, J = 8.4 Hz, 2.1 Hz, 1H), 7.70 (dd, J = 7.5 Hz, 1.8 Hz, 1H) |
| 10 | (2d) | | 1.39 (d, J = 6.3 Hz, 6H), 1.47 (t, J = 6.9 Hz, 3H), 2.99 (t, J = 7.5 Hz, 2H), 3.42 (t, J = 7.5 Hz, 2H), 3.89 (s, 3H), 4.13 (q, J = 6.9 Hz, 2H), 4.60-4.66 (m, 1H), 6.89-7.00 (m, 3H), 7.39-7.45 (m, 2H), 7.54-7.59 (m, 2H), 7.70 (dd, J = 7.5 Hz, 1.8 Hz, 1H) |
| 11 | (2e) | | 1.45-1.51 (m, 6H), 2.99 (t, J = 6.9 Hz, 2H), 3.42 (t, J = 6.9 Hz, 2H), 3.91 (s, 3H), 4.09-4.21 (m, 4H), 6.89-6.99 (m, 3H), 7.40-7.52 (m, 2H), 7.56 (dd, J = 8.4 Hz, 1.8 Hz, 1H), 7.70 (dd, J = 7.5 Hz, 1.8 Hz, 1H) |
| 12 | (2f) | | 1.47 (t, J = 6.9 Hz, 3H), 2.99 (t, J = 7.2 Hz, 2H), 3.42 (t, J = 7.2 Hz, 2H), 3.92 (s, 3H), 4.13 (q, J = 6.9 Hz, 2H), 4.67 (d, J = 5.1 Hz, 2H), 5.29-5.47 (m, 2H), 6.05-6.18 (m, 1H), 6.90-7.00 (m, 3H), 7.40-7.45 (m, 2H), 7.52 (d, J = 1.8 Hz, 1H), 7.58 (dd, J = 8.4 Hz, 1.8 Hz, 1H) 7.70 (dd, J = 1.8 Hz, 7.8 Hz, 1H) |

TABLE 2-continued

| Example | Compound | Structural formula | $^1$H NMR (CDCl$_3$, 300 MHz) |
|---|---|---|---|
| 13 | (2g) | | 0.35-0.40 (m, 2H), 0.63-0.69 (m, 2H), 1.32-1.41 (m, 1H), 2.49 (s, 3H), 3.00 (t, J = 7.2 Hz, 2H), 3.32 (t, J = 7.2 Hz, 2H), 3.92 (s, 3H), 3.93 (d, J = 6.9 Hz, 2H), 6.91 (d, J = 8.1 Hz, 1H), 7.22-7.25 (m, 2H), 7.36 (td, J = 7.5 Hz, 1.5 Hz, 1H), 7.43 (t, J = 0.9 Hz, 1H), 7.49 (d, J = 2.1 Hz, 1H), 7.57 (dd, J = 8.1 Hz, 2.1 Hz, 1H), 7.68 (dd, J = 7.5 Hz, 1.5 Hz, 1H) |
| 14 | (2h) | | 0.35-0.41 (m, 2H), 0.62-0.69 (m, 2H), 1.32-1.40 (m, 1H), 2.57 (s, 3H), 3.00 (t, J = 7.5 Hz, 2H), 3.60 (t, J = 7.5 Hz, 2H), 3.91-3.94 (m, 5H), 6.91 (d, J = 8.7 Hz, 1H), 7.29-7.34 (m, 1H), 7.45 (s, 1H), 7.49 (d, J = 1.8 Hz, 1H), 7.54-7.60 (m, 2H), 8.50 (dd, J = 4.5 Hz, 1.2 Hz, 1H) |
| 15 | (2i) | | 1.49 (t, J = 7.2 Hz, 3H), 2.57 (s, 3H), 3.00 (t, J = 7.2 Hz, 2H), 3.59 (t, J = 7.2 Hz, 2H), 3.91 (s, 3H), 4.19 (q, J = 7.2 Hz, 2H), 6.90 (d, J = 8.4 Hz, 1H), 7.45 (s, 1H), 7.51 (d, J = 2.1 Hz, 1H), 7.55-7.58 (m, 2H), 8.24 (d, J = 4.2 Hz, 1H) |
| 16 | (2j) | | 2.57 (s, 3H), 3.00 (t, J = 7.2 Hz, 2H), 3.60 (t, J = 7.2 Hz, 2H), 3.92 (s, 3H), 4.66-4.69 (m, 2H), 5.28-5.48 (m, 2H), 6.05-6.16 (m, 1H), 6.92 (d, J = 8.7 Hz, 1H), 7.29-7.34 (m, 1H), 7.45 (s, 1H), 7.52 (d, J = 2.1 Hz, 1H), 7.56-7.60 (m, 2H), 8.48-8.51 (m, 1H) |
| 17 | (2k) | | 1.84-2.00 (m, 4H), 2.13-2.22 (m, 2H), 2.57 (s, 3H), 2.83-2.89 (m, 1H), 3.01 (t, J = 7.5 Hz, 2H), 3.60 (t, J = 7.5 Hz, 2H), 3.89 (s, 3H), 4.07 (d, J = 6.9 Hz, 2H), 6.89 (d, J = 8.7 Hz, 1H), 7.29-7.34 (m, 1H), 7.45 (d, J = 2.1 Hz, 1H), 7.51-7.60 (m, 3H), 8.50 (dd, J = 4.5 Hz, 1.2 Hz, 1H) |

Example 18

Synthesis of Compound (12a)

Compound (12a) was produced according to the following reactions.

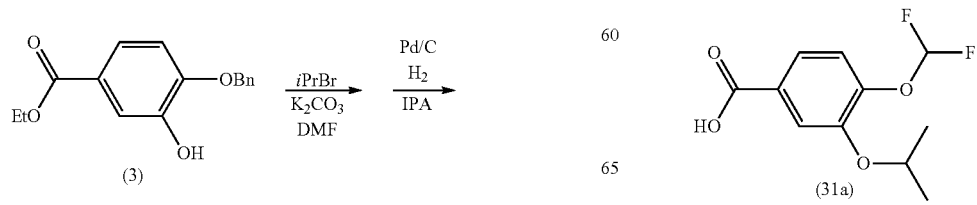

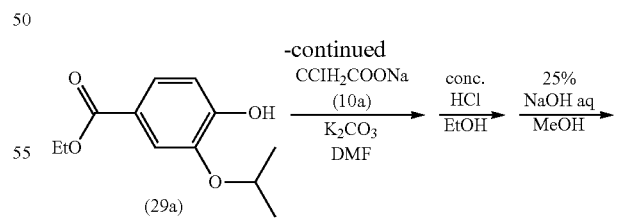

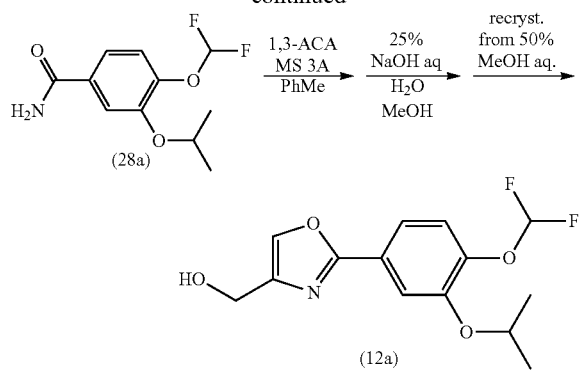

(18-1) Synthesis of Compound (29a)

Compound (3) (50.0 g, 184 mmol), DMF (200 ml), and potassium carbonate (50.8 g, 2 eq.) were introduced into a reaction vessel. Isopropyl bromide (34.5 ml, 2 eq.) was added thereto, and the mixture was heated under stirring at about 80° C. for 3 hours. After the mixture was cooled to room temperature, water (300 ml) was added thereto to dissolve inorganic salt. EtOAc (300 ml) was then added thereto, and extraction and liquid separation was performed. The organic layer was washed with water (500 ml), and then concentrated to dryness to obtain an oily product of ethyl 4-(benzyloxy)-3-isopropoxybenzoate. The resulting oil and IPA (100 ml) were added to a pressurized vessel. Subsequently, 5% Pd—C (wet) (1.00 g) was added thereto, and $H_2$ gas (theoretical amount: 1 eq.) was absorbed at room temperature. After the completion of the absorption, the catalyst was removed by filtration, and the filtrate was concentrated to dryness. MeOH (50 ml) and water (100 ml) were added to the concentrated reaction mixture, followed by cooling and aging. The precipitated crystals were collected by filtration, and dried at 40° C. to give Compound (29a) (39.4 g).

Compound (29a):

$^1$H NMR (CDCl$_3$, 400 MHz) δ 1.35 (t, J=7.3 Hz, 3H), 1.36 (d, J=6.4 Hz, 6H), 4.32 (q, J=7.3 Hz, 2H), 4.67 (sept, J=6.4 Hz, 1H), 6.08 (s, 1H), 6.92 (d, J=8.3 Hz, 1H), 7.53 (d, J=1.8 Hz, 1H), 7.60 (dd, J=8.3 Hz, 1.8 Hz, 1H).

(18-2) Synthesis of Compound (31a)

Compound (29a) (148 g, 660 mmol), sodium chlorodifluoroacetate (121 g, 1.2 eq.), and potassium carbonate (109 g, 1.2 eq.) were added to DMF (1480 ml), and the mixture was heated under stirring at about 90° C. for 2 hours. After the mixture was cooled to room temperature, inorganic salt was removed by filtration. AcOEt (1480 ml) and water (1480 ml) were added thereto, and extraction and liquid separation was performed. The water layer was again extracted with AcOEt (740 ml). The collected organic layer was concentrated to dryness to obtain an oily product. EtOH (740 ml) was added to the resulting oil and dissolved, and concentrated hydrochloric acid (148 ml) was added thereto, followed by heating at reflux for one hour. After the completion of the reaction, EtOH was distilled off, and then water (740 ml), toluene (1480 ml) and a 25% NaOH aqueous solution (148 ml) were added to the residue, and extraction and liquid separation was performed. After the organic layer was washed with water (740 ml), it was concentrated to dryness to obtain an oily product. MeOH (592 ml) was added to the resulting oil and dissolved, and a 25% NaOH aqueous solution (104 ml) was added, followed by heating at reflux for one hour. After the resultant was cooled to 30° C. or less, water (888 ml) and concentrated hydrochloric acid (74.0 ml) were added thereto, followed by cooling and aging. The precipitated crystals were collected by filtration and dried at 60° C. to give Compound (31a) (95.1 g).

Compound (31a):

$^1$H NMR (CDCl$_3$, 400 MHz) δ 1.38 (d, J=6.0 Hz, 6H), 4.65 (sept, J=6.0 Hz, 1H), 6.65 (t, J=75 Hz, 1H), 7.21 (d, J=8.7 Hz, 1H), 7.68 (d, J=2.0 Hz, 1H), 7.69 (dd, J=8.7 Hz, 2.0 Hz, 1H).

(18-3) Synthesis of Compound (28a)

Compound (31a) (87.0 g, 353 mmol) was added to acetonitrile (261 ml), and then CDI (1,1'-carbodiimidazole) (68.8 g, 1.2 eq.) was added thereto. The mixture was stirred at room temperature for one hour to obtain an active ester solution. The solution was added to a mixed solution of water (1044 ml) and 25% aqueous ammonia (87.0 ml), and stirred at 0° C. for 2 hours to collect a precipitated crystal by filtration. The obtained crystal was dried at 60° C. to give Compound (28a) (79.5 g).

Compound (28a):

$^1$H NMR (CDCl$_3$, 400 MHz) δ 1.36 (d, J=6.0 Hz, 6H), 4.65 (sept, J=6.0 Hz, 1H), 5.64 (br-s, 1H), 6.03 (br-s, 1H), 6.61 (t, J=75 Hz, 1H), 7.17 (d, J=8.3 Hz, 1H), 7.23 (dd, J=8.3 Hz, 1.8 Hz, 1H), 7.53 (d, J=1.8 Hz, 1H).

(18-4) Synthesis of Compound (12a)

Toluene (50.0 ml) was added to Compound (28a) (50.0 g, 204 mmol) and molecular sieves 3A (MS 3A) (50.0 g), and 1-acetoxy 3-chloroacetone (1,3-ACA) (36.0 ml, 1.5 eq.) was added thereto, followed by heating at reflux for 22 hours. After toluene (100 ml) was added and the mixture was cooled to room temperature, MS 3A was removed by filtration. Toluene (250 ml), water (100 ml), and a 25% NaOH aqueous solution (25 ml) were added to the resulting solution, and extraction and liquid separation was performed. The resulting organic layer was concentrated to dryness to obtain an oily product. The resulting oil was dissolved in MeOH (250 ml), and water (200 ml) and a 25% NaOH aqueous solution (50 ml) were added thereto, followed by heating at reflux for 15 minutes. After the resulting mixture was cooled, the precipitated crystals were collected by filtration and dried at 80° C. to obtain a crude product of Compound (12a). The crude product was heated and dissolved in MeOH (100 ml), and water (100 ml) was added thereto. After the reaction mixture was cooled, the precipitated crystals were collected by filtration and dried at 80° C. to give Compound (12a) (49.6 g).

Compound (12a):

$^1$H NMR (CDCl$_3$, 400 MHz) δ 1.40 (d, J=6.0 Hz, 6H), 2.33 (br-s, 1H), 4.68 (d, J=5.5 Hz, 2H), 4.70 (sept, J=6.0 Hz, 1H), 6.62 (t, J=75 Hz, 1H), 7.22 (d, J=8.2 Hz, 1H), 7.59 (dd, J=8.2 Hz, 1.8 Hz, 1H), 7.64 (s, 1H), 7.66 (d, J=1.8 Hz, 1H).

Example 19

Synthesis of Compound (12b)

Compound (12b) was produced according to the following reactions.

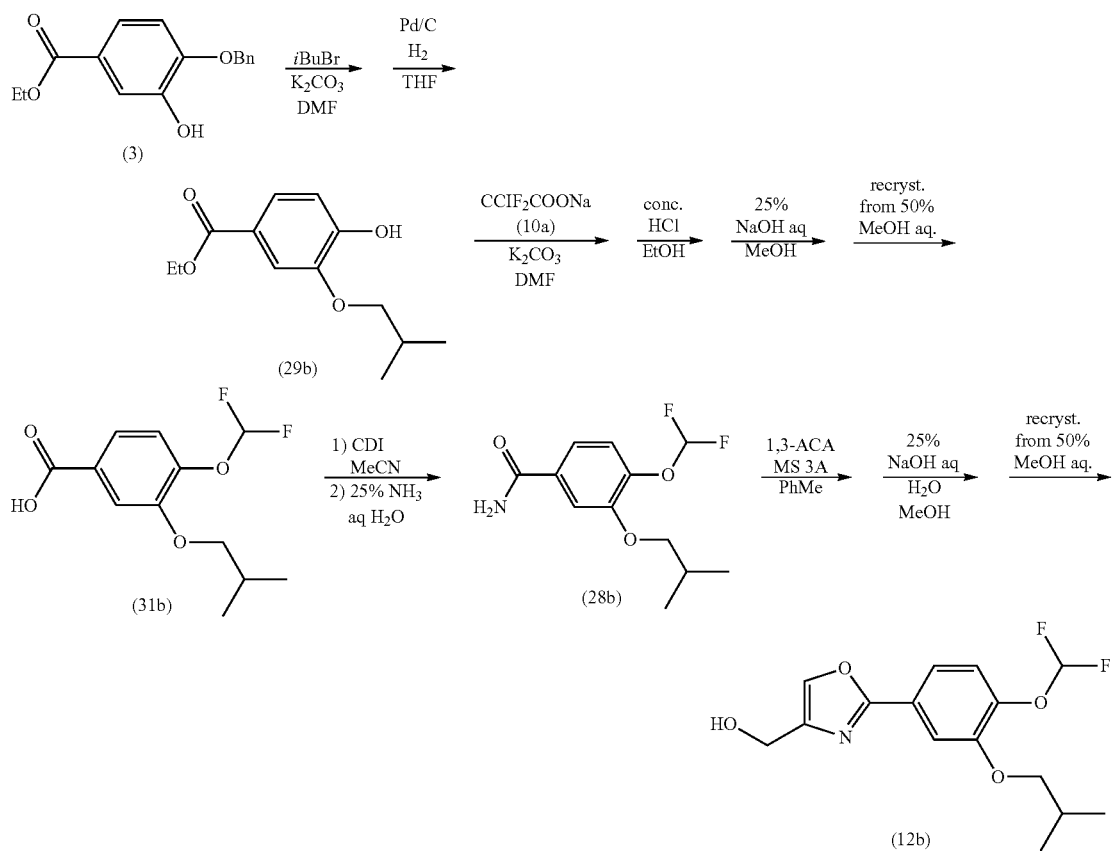

Compound (29b):

$^1$H NMR (CDCl$_3$, 400 MHz) δ 1.03 (d, J=6.4 Hz, 6H), 1.36 (t, J=7.2 Hz, 3H), 2.13 (sept, J=6.4 Hz, 1H), 3.85 (d, J=6.4 Hz, 2H), 4.33 (q, J=7.2 Hz, 1H), 6.92 (d, J=8.0 Hz, 1H), 7.50 (d, J=2.0 Hz, 1H), 7.61 (dd, J=8.0 Hz, 2.0 Hz, 1H).

(19-1) Synthesis of Compound (29b)

Compound (3) (48.0 g, 176 mmol), DMF (192 ml), potassium carbonate (48.8 g, 2 eq.) were introduced into a reaction vessel. Isobutyl bromide (38.3 ml, 2 eq.) was added thereto, and the mixture was heated under stirring at about 80° C. for 2 hours. After the mixture was cooled to room temperature, water (288 ml) was added, and inorganic salt was dissolved. Thereafter, EtOAc (288 ml) was added thereto, and extraction and liquid separation was performed. After the organic layer was washed with water (480 ml), it was concentrated to dryness to obtain an oily product of ethyl 4-(benzyloxy)-3-isobutoxybenzoate. The resulting oil and THF (96 ml) were added to a pressurized vessel. 5% Pd—C (wet) (960 mg) was added thereto, and H$_2$ gas (theoretical amount: 1 eq.) was absorbed at room temperature. After the completion of the absorption, the catalyst was removed by filtration, and the filtrate was concentrated to dryness. MeOH (48 ml) and water (96 ml) were added to the concentrated reaction mixture, followed by cooling and aging. The precipitated crystals were then collected by filtration and dried at 40° C. to give Compound (29b) (41.2 g.

(19-2) Synthesis of Compound (31b)

DMF (390 ml) was added to compound (29b) (39.0 g, 164 mmol), sodium chlorodifluoroacetate (29.9 g, 1.2 eq.), and potassium carbonate (45.2 g, 2 eq.), and the mixture was heated under stirring at about 90° C. for 2 hours. After the mixture was cooled to room temperature, inorganic salt was removed by filtration, AcOEt (312 ml) and water (312 ml) were added thereto, and extraction and liquid separation was performed. After the water layer was again extracted with AcOEt (195 ml), the collected organic layer was concentrated to dryness to obtain an oily product. EtOH (195 ml) was added to the resulting oil and dissolved, and concentrated hydrochloric acid (19.5 ml) was added thereto, and heated at reflux for one hour. After the completion of the reaction, EtOH was distilled off, and then water (195 ml), toluene (351 ml), and a 25% NaOH aqueous solution (39 ml) were added to the residue, and extraction and liquid separation was performed. After the organic layer was washed with water (195 ml), it was concentrated to dryness to obtain an oily product. MeOH (156 ml) was added to the resulting oil and dissolved, and a 25% NaOH aqueous solution (27 ml) was added thereto, followed by heating at reflux for one hour. After the resultant was cooled to 30° C. or less, water (234 ml) and concentrated hydrochloric acid (20 ml) were added thereto, followed by cooling and aging. The precipitated crystals were then collected by filtration and dried at 60° C. to obtain a crude product (24.7 g) of Compound (31b). The crude product was dissolved in MeOH (25 ml) by heating, and water (25 ml) was added thereto, followed by cooling and aging. A precipitated crystal was then collected by filtration, and the obtained crystal was dried at 60° C. to give Compound (31b) (22.8 g).

Compound (31b):

$^1$H NMR (CDCl$_3$, 400 MHz) δ 1.03 (d, J=6.4 Hz, 6H), 2.15 (sept, J=6.4 Hz, 1H), 3.83 (d, J=6.4 Hz, 2H), 6.64 (t, J=74 Hz, 1H), 7.21 (d, J=8.4 Hz, 1H), 7.65 (d, J=2.0 Hz, 1H), 7.70 (dd, J=8.4 Hz, 2.0 Hz, 1H).

(19-3) Synthesis of Compound (28b)

Compound (31b) (22.4 g, 75.2 mmol) was added to acetonitrile (112 ml), and then CDI (1,1'-carbodiimidazole) (16.7 g, 1.2 eq.) was added thereto. The mixture was stirred at room temperature for one hour to obtain an active ester solution. The solution was added to a mixed solution of water (267 ml) and 25% aqueous ammonia (45 ml), followed by stirring at 0° C. for one hour. The precipitated crystals were collected by filtration. The obtained crystals were dried at 60° C. to give Compound (28b) (20.2 g).

Compound (28b):

$^1$H NMR (CDCl$_3$, 400 MHz) δ 1.03 (d, J=6.4 Hz, 6H), 2.13 (sept, J=6.4 Hz, 1H), 3.83 (d, J=6.4 Hz, 2H), 5.58 (br-s, 1H), 6.01 (br-s, 1H), 6.61 (t, J=75 Hz, 1H), 7.18 (d, J=8.0 Hz, 1H), 7.23 (dd, J=8.0 Hz, 2.0 Hz, 1H), 7.51 (d, J=2.0 Hz, 1H).

(19-4) Synthesis of Compound (12b)

Compound (28b) (19.5 g, 86.1 mmol) and molecular sieves 3A (MS 3A) (19.5 g) were added to toluene (20 ml). 1-Acetoxy-3-chloroacetone (1,3-ACA) (13.3 ml, 1.5 eq.) was added thereto, followed by heating at reflux for 15 hours. After toluene (39 ml) was added thereto and the mixture was cooled to room temperature, MS 3A was removed by filtration. Toluene (98 ml), water (98 ml), and a 25% NaOH aqueous solution (20 ml) were added to the resulting solution, and extraction and liquid separation was performed. The resulting organic layer was concentrated to dryness to obtain an oily product. The resulting oil was dissolved in MeOH (98 ml), and water (78 ml) and a 25% NaOH aqueous solution (20 ml) were added thereto, followed by heating at reflux for 15 minutes. After the resulting mixture was cooled, the precipitated crystals were collected by filtration and dried at 80° C. to obtain a crude product of Compound (12b) (20.2 g). The crude product was dissolved by heating in MeOH (78 ml), and water (78 ml) was added. After the mixture was cooled, the precipitated crystals were collected by filtration and dried at 80° C. to give Compound (12b) (19.4 g).

Compound (12b):

$^1$H NMR (CDCl$_3$, 400 MHz) δ1.04 (d, J=6.4 Hz, 6H), 2.15 (sept, J=6.4 Hz, 1H), 3.85 (d, J=6.4 Hz, 2H), 4.66 (s, 2H), 6.60 (t, J=75.1 Hz, 1H), 7.21 (d, J=8.2 Hz, 1H), 7.56 (dd, J=8.2 Hz, 1.8 Hz, 1H), 7.61 (d, J=1.8 Hz, 1H), 7.63 (s, 1H).

Example 20

Compound (1a) was produced according to the following reactions.

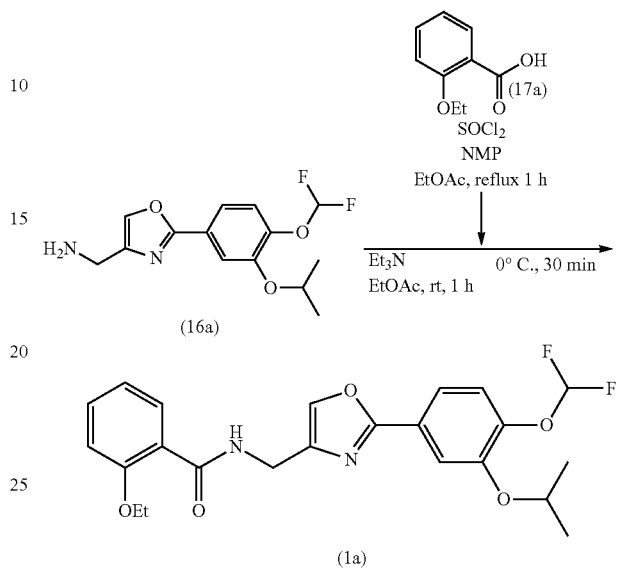

Synthesis of Compound (1a)

Compound (16a) (10.0 g, 29.9 mmol) was added to AcOEt (100 ml), and then triethylamine (15.1 ml, 3.6 eq.) was added thereto, followed by stirring at room temperature for one hour. The solution was cooled to about 0° C. Separately, N-methylpyrrolidone (200 µl) and AcOEt (50 ml) were added to 2-ethoxybenzoic acid (5.95 g, 1.2 eq.), and then thionyl chloride (2.83 ml, 1.3 eq.) was added thereto, followed by heating at reflux for one hour to prepare a solution of 2-ethoxybenzoyl chloride. The solution of 2-ethoxybenzoyl chloride was added at 0° C. to the Compound (16a)-containing solution, which had been obtained as above, followed by stirring at the same temperature for 30 minutes. After the completion of the reaction, water (50 ml) and concentrated hydrochloric acid (5 ml) were added thereto, and extraction and liquid separation was performed. Subsequently, the organic layer was washed with water (50 ml) and a 25% NaOH aqueous solution (5 ml), and concentrated to dryness to obtain an oily product. EtOH (50 ml) and water (20 ml) were added to the oily product, followed by dissolution, and a seed crystal was added thereto, followed by cooling and aging. The precipitated crystals were then collected by filtration, and dried at 45° C. to give Compound (1a) (9.70 g).

Compound (1a):

$^1$H NMR (CDCl$_3$, 400 MHz) δ 1.40 (d, J=6.0 Hz, 6H), 1.49 (t, J=6.9 Hz, 3H), 4.19 (q, J=6.9 Hz, 2H), 4.63 (d, J=5.5 Hz, 2H) 4.69 (sept, J=6.0 Hz, 1H), 6.63 (t, J=75 Hz, 1H), 6.95 (d, J=8.2 Hz, 1H), 7.08 (t, J=7.8 Hz, 1H), 7.23 (d, J=8.2 Hz 1H), 7.43 (td, J=8.0, 1.4 Hz, 1H), 7.59 (dd, J=8.2, 1.8 Hz, 1H) 7.67 (d, J=1.8 Hz, 1H), 7.67 (s, 1H), 8.24 (dd, J=7.8, 1.8 Hz, 1H), 8.56 (br-s, 1H).

Example 21

Compound (1b) was produced according to the following reactions.

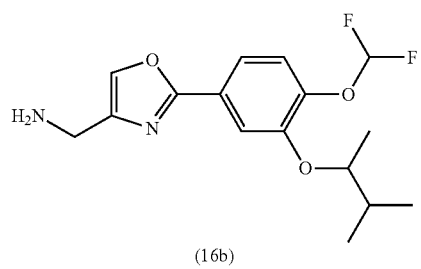

(16b)

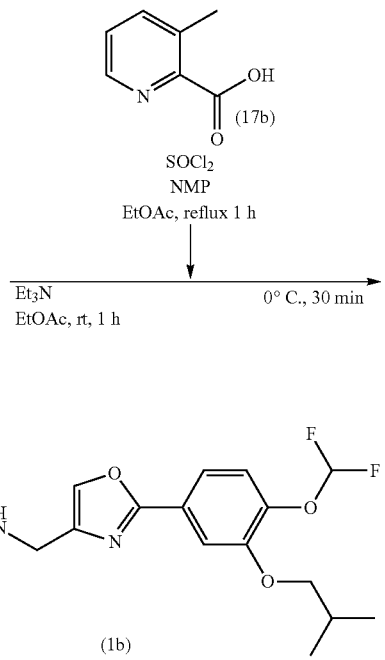

Synthesis of Compound (1b)

Compound (1b) was obtained by the treatment according to Example 20, except that Compound (16b) and (17b) were used in place of Compound (16a) and (17a).

Compound (1b):

$^1$H NMR (CDCl$_3$, 400 MHz) δ 1.04 (d, J=6.9 Hz, 6H), 2.14 (sept, J=6.9 Hz, 1H), 2.74 (s, 3H), 3.86 (d, J=6.9 Hz, 2H), 4.58 (d, J=5.5 Hz, 2H), 6.60 (t, J=75 Hz, 1H), 7.20 (d, J=8.2 Hz, 1H), 7.30 (dd, J=8.0, 4.6 Hz, 1H), 7.56 (dd, J=8.2, 1.8 Hz, 2H), 7.60 (d, J=1.8 Hz, 1H), 7.66 (s, 1H), 8.38 (dd, J=4.6, 1.4 Hz 1H), 8.59 (br-s, 1H).

Since the production method of the present invention does not use a dihaloketone compound, which is harmful to humans, throughout the production processes thereof, it is preferable from the viewpoint of the health and/or safety of the people who are involved in its production. Furthermore, since this method allows purification without using column chromatography throughout the production process, it is an effective method on an industrial scale.

The invention claimed is:

1. A compound represented by formula (12):

wherein R$^1$ is lower alkyl group or halogen substituted lower alkyl group, and R$^2$ is lower alkyl group.

2. The compound according to claim 1, wherein in formula (12), R$^1$ is methyl or difluoromethyl group, and R$^2$ is methyl, isopropyl, or isobutyl group.

3. A method for producing a compound represented by formula (12),

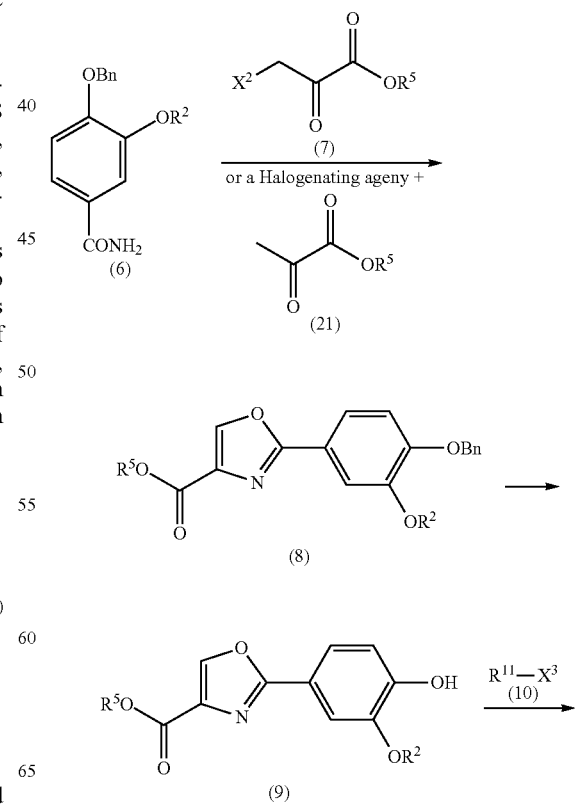

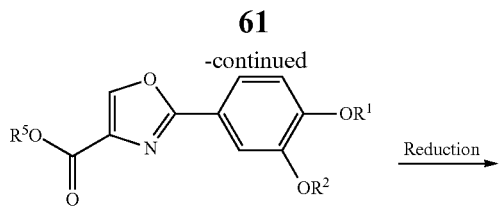

wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group, or a group represented by formula: $-CY_2COOR^{12}$, wherein Y is a halogen atom, $R^{12}$ is an alkali metal atom or lower alkyl group, and $X^2$ and $X^3$ are the same or different and are halogen atoms, the method comprising the steps of:

(a) reacting a compound represented by formula (6) with a compound represented by formula (7), or with a halogenating agent and a compound represented by formula (21) to obtain a compound represented by formula (8);
(b) debenzylating the compound represented by formula (8) to obtain a compound represented by formula (9);
(c) reacting the compound represented by formula (9) with a compound represented by formula (10) in the presence of a base to obtain a compound represented by formula (11); and
(d) reducing the compound represented by formula (11) to obtain the compound represented by formula (12).

4. The method for producing a compound represented by formula (12) according to claim 3,

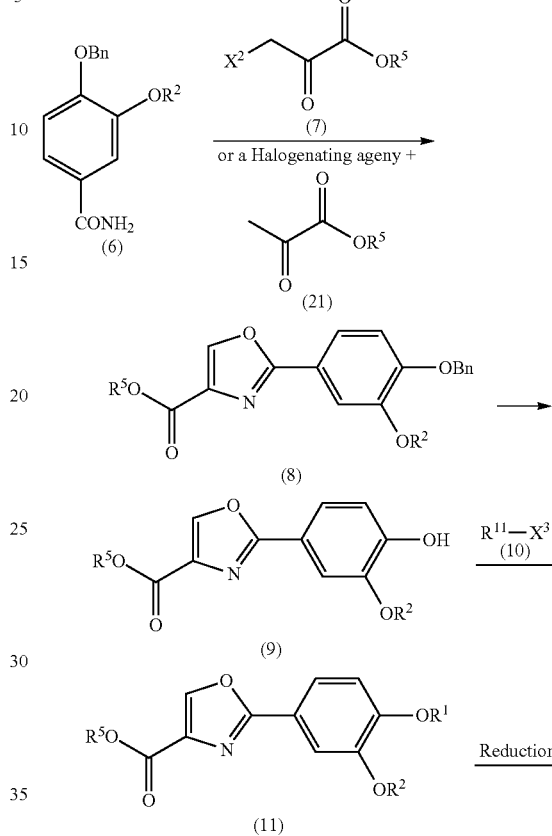

wherein $X^1$ is a halogen atom and $R^2$ is as defined above, the compound represented by formula (6) being produced by the process comprising the steps of:

(a') reacting a compound represented by formula (3) with a compound represented by formula (4) in the presence of a base to obtain a compound represented by formula (3');
(b') hydrolyzing a compound represented by formula (3') to obtain a compound represented by formula (5); and
(c') subjecting the compound represented by formula (5) to a condensation reaction with ammonia (amidation) to obtain the compound represented by formula (6).

5. A method for producing a compound represented by formula (1),

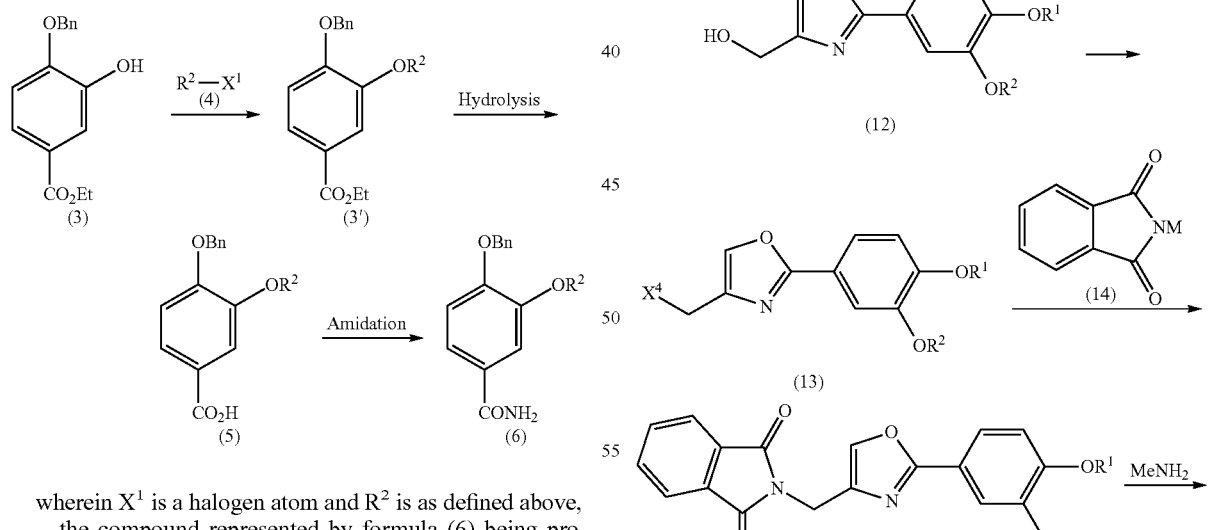

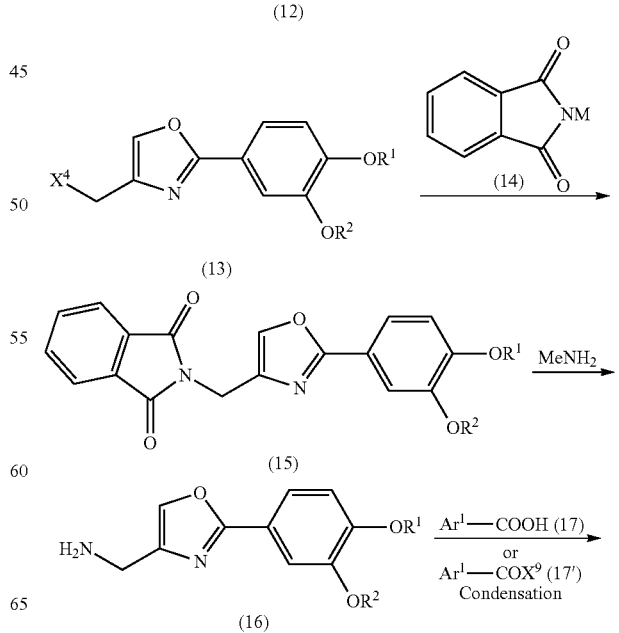

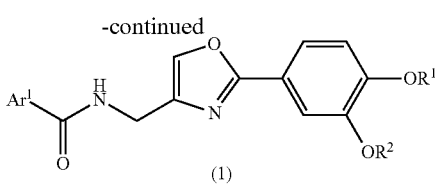

wherein $R^1$ is lower alkyl group or halogen substituted lower alkyl group, $R^2$ is lower alkyl group, $R^5$ is lower alkyl group, $R^{11}$ is lower alkyl group, halogen substituted lower alkyl group or a group represented by formula: $-CY_2COOR^{12}$, wherein Y is a halogen atom, $R^{12}$ is an alkali metal atom or lower alkyl group, $Ar^1$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group, $X^2$, $X^3$ and $X^9$ are the same or different and are halogen atoms, $X^4$ is a leaving group, and M is an alkali metal atom, the method comprising the steps of:

(a) reacting a compound represented by formula (6) with a compound represented by formula (7), or with a halogenating agent and a compound represented by formula (21) to obtain a compound represented by formula (8);

(b) debenzylating the compound represented by formula (8) to obtain a compound represented by formula (9);

(c) reacting the compound represented by formula (9) with a compound represented by formula (10) in the presence of a base to obtain a compound represented by formula (11);

(d) reducing the compound represented by formula (11) to obtain a compound represented by formula (12);

(e) converting the hydroxyl group of the compound represented by formula (12) into a leaving group ($X^4$) to obtain a compound represented by formula (13);

(f) reacting the compound represented by formula (13) with a compound represented by formula (14) to obtain a compound represented by formula (15), (g) reacting the compound represented by formula (15) with methylamine to obtain a compound represented by formula (16); and (h) subjecting the compound represented by formula (16) to a condensation reaction with a compound represented by formula (17) or with a compound represented by formula (17') to obtain the compound represented by formula (1).

6. A method for producing a compound represented by formula (1),

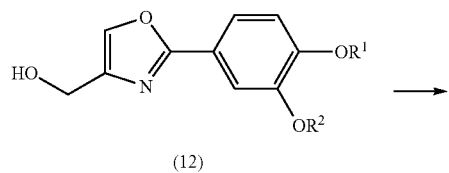

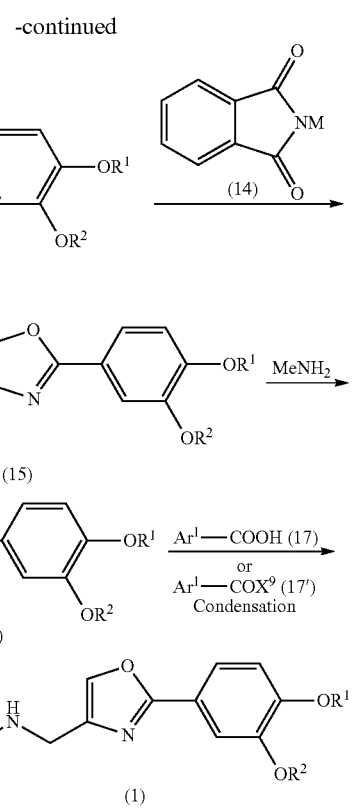

wherein $R^1$ is lower alkyl group or halogen substituted lower alkyl group, $R^2$ is lower alkyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^9$ is a halogen atom, $X^4$ is a leaving group, and M is an alkali metal atom, the method comprising the steps of:

(e) converting the hydroxyl group of the compound represented by formula (12) into a leaving group ($X^4$) to obtain a compound represented by formula (13);

(f) reacting the compound represented by formula (13) with a compound represented by formula (14) to obtain a compound represented by formula (15);

(g) reacting the compound represented by formula (15) with methylamine to obtain a compound represented by formula (16); and (h) subjecting the compound represented by formula (16) to a condensation reaction with a compound represented by formula (17) or with a compound represented by formula (17') to obtain the compound represented by formula (1).

7. A method for producing a compound represented by formula (12),

65

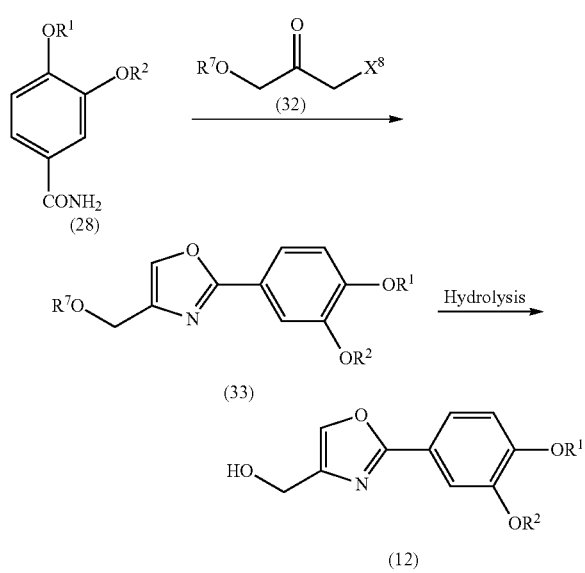

wherein $R^1$ is lower alkyl group or halogen substituted lower alkyl group, $R^2$ is lower alkyl group, $R^7$ is lower alkanoyl group, and $X^8$ is a halogen atom, the method comprising the steps of:
(a) reacting the compound represented by formula (28) with a compound represented by formula (32) to obtain a compound represented by formula (33); and
(b) hydrolyzing the compound represented by formula (33) to obtain the compound represented by formula (12).

8. The method for producing a compound represented by formula (12) according to claim 7,

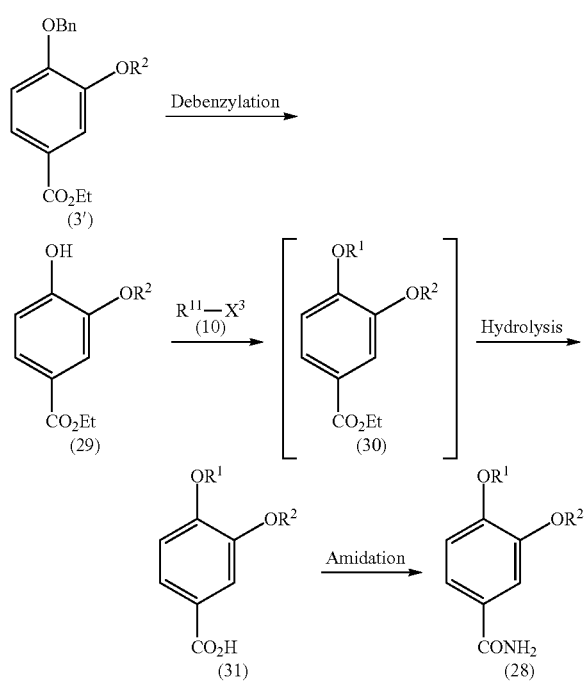

wherein $R^{11}$ is lower alkyl group, halogen substituted lower alkyl group or a group represented by formula: —$CY_2COOR^{12}$, wherein Y is a halogen atom, $R^{12}$ is an alkali metal atom or lower alkyl group, $X^3$ is a halogen atom, and $R^1$ and $R^2$ are as defined above, the compound represented by formula (28) being produced by the process comprising the steps of:
(a') debenzylating the compound represented by formula (3') to obtain a compound represented by formula (29);
(b') reacting the compound represented by formula (29) with a compound represented by formula (10) in the presence of a base to obtain a compound represented by formula (30);
(c') hydrolyzing the compound represented by formula (30) to obtain a compound represented by formula (31); and
(d') subjecting the compound represented by formula (31) to a condensation reaction with ammonia (amidation) to obtain the compound represented by formula (28).

9. A method for producing a compound represented by formula (1),

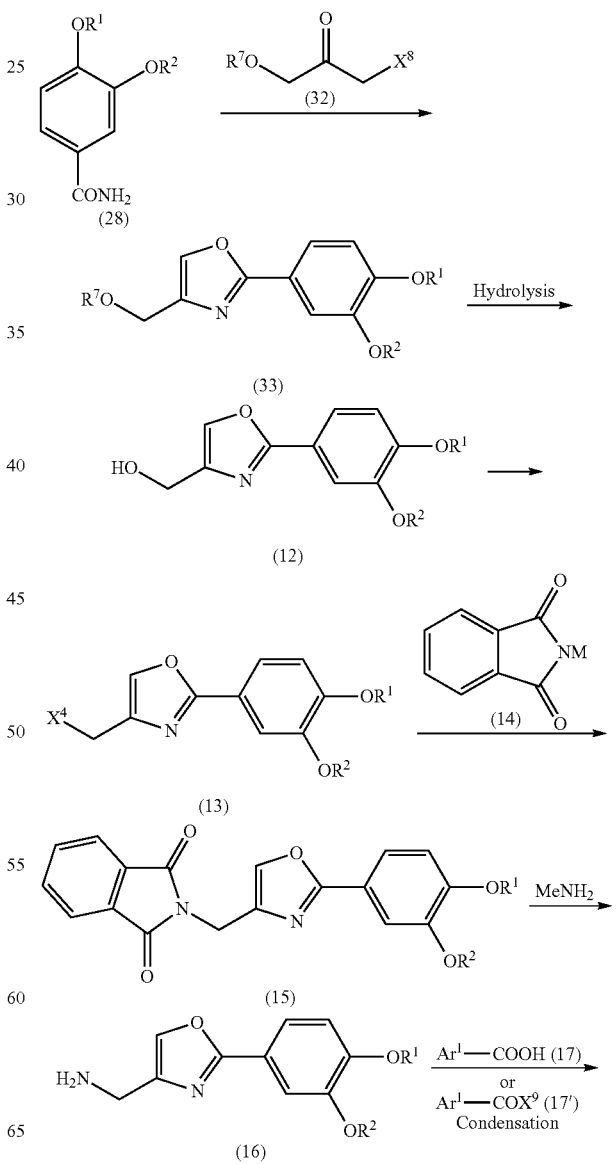

-continued

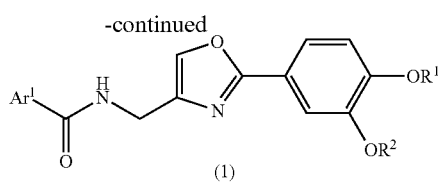

(1)

-continued

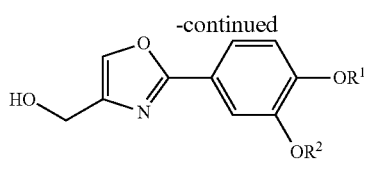

(12)

wherein $R^1$ is lower alkyl group or halogen substituted lower alkyl group, $R^2$ is lower alkyl group, $R^7$ is lower alkanoyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^4$ is a leaving group, $X^8$ and $X^9$ are the same or different and are halogen atoms, and M is an alkali metal atom, the method comprising the steps of:
(a) reacting the compound represented by formula (28) with a compound represented by formula (32) to obtain a compound represented by formula (33);
(b) hydrolyzing the compound represented by formula (33) to obtain a compound represented by formula (12);
(c) converting the hydroxyl group of the compound represented by formula (12) into a leaving group ($X^4$) to obtain a compound represented by formula (13);
(d) reacting the compound represented by formula (13) with a compound represented by formula (14) to obtain a compound represented by formula (15);
(e) reacting methylamine with the compound represented by formula (15) to obtain a compound represented by formula (16); and
(f) subjecting the compound represented by formula (16) to a condensation reaction with a compound represented by formula (17) or with a compound represented by formula (17') to obtain the compound represented by formula (1).

10. A method for producing a compound represented by formula (1),

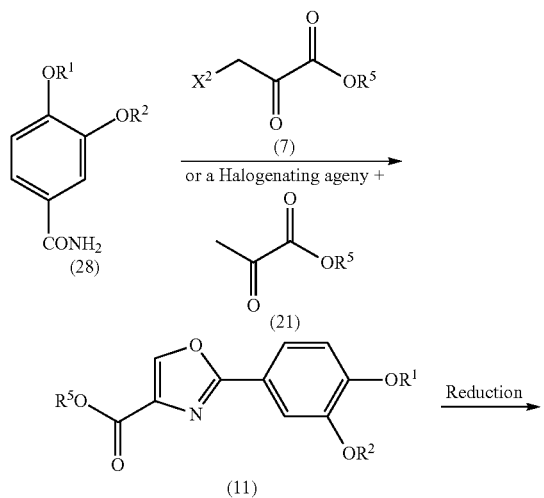

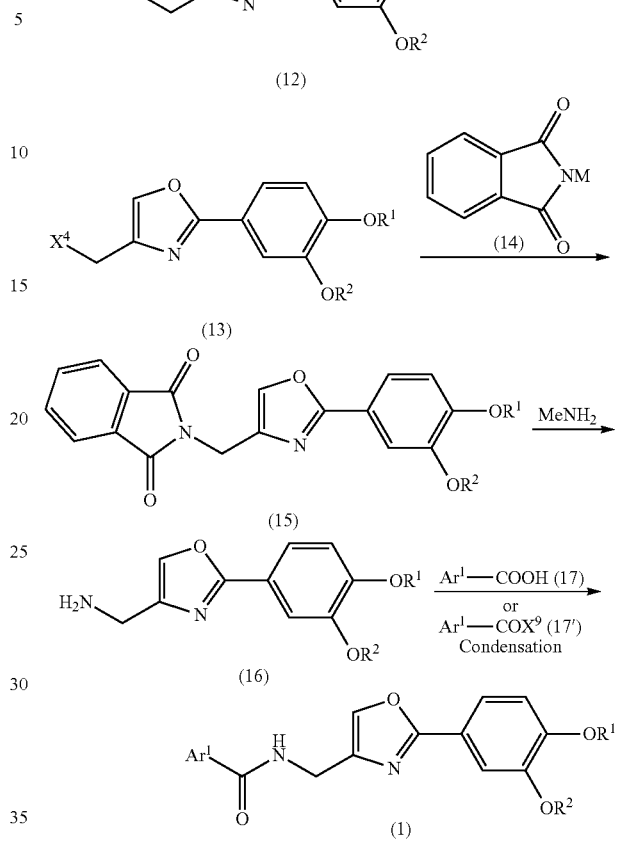

wherein $R^1$ is lower alkyl group or halogen substituted lower alkyl group, $R^2$ is lower alkyl group, $R^5$ is lower alkyl group, $Ar^1$ is phenyl group substituted with at least one substituent selected from the group consisting of lower alkyl group, halogen substituted lower alkyl group, lower alkoxy group and halogen substituted lower alkoxy group, or a pyridyl group substituted with at least one substituent selected from the group consisting of lower alkyl group, halogen substituted lower alkyl group, lower alkoxy group and halogen substituted lower alkoxy group, $X^2$ and $X^9$ are the same or different and are halogen atoms, $X^4$ is a leaving group, and M is an alkali metal atom, the method comprising the steps of:
(a) reacting a compound represented by formula (28) with a compound represented by formula (7) or with a halogenating agent and the compound represented by formula (21) to obtain a compound represented by formula (11);
(b) reducing the compound represented by formula (11) to obtain a compound represented by formula (12);
(c) converting the hydroxyl group of the compound represented by formula (12) into a leaving group ($X^4$) to obtain a compound represented by formula (13);
(d) reacting the compound represented by formula (13) with a compound represented by formula (14) to obtain a compound represented by formula (15);
(e) reacting the compound represented by formula (15) with methylamine to obtain a compound represented by formula (16); and (f) subjecting the compound represented by formula (16) to a condensation reaction with a compound represented by formula (17) or with a compound represented by formula (17') to obtain the compound represented by formula (1).

11. A method for producing a compound represented by formula (2),

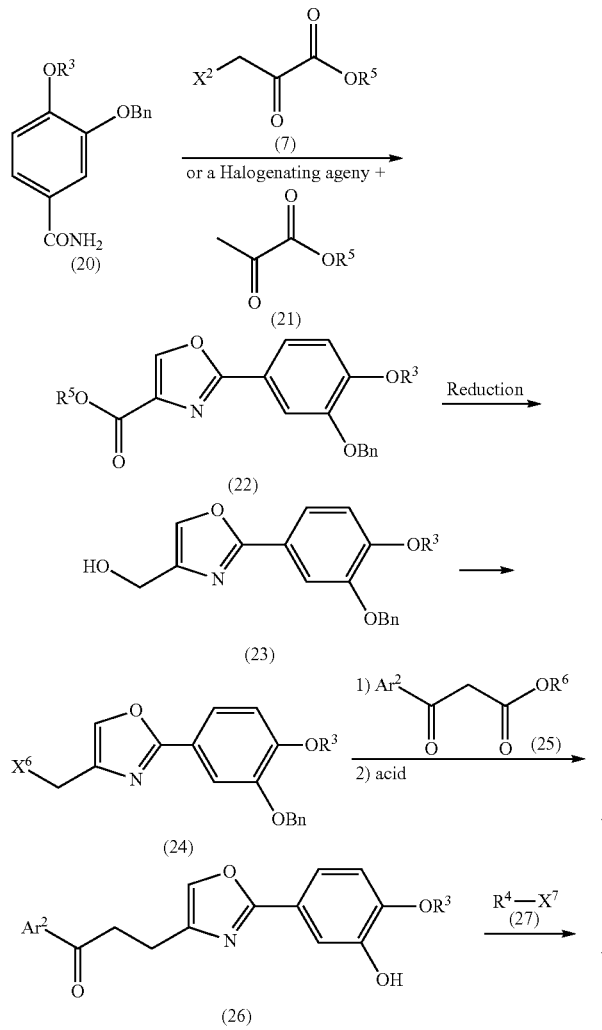

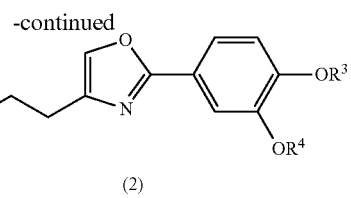

wherein $R^3$ is lower alkyl group or halogen substituted lower alkyl group, $R^4$ is lower alkyl group, cycloalkyl-lower alkyl group, or lower alkenyl group, $R^5$ is lower alkyl group, $R^6$ is lower alkyl group, $Ar^2$ is phenyl group substituted with at least one substituent selected from the group consisting of lower alkyl group, halogen substituted lower alkyl group, lower alkoxy group and halogen substituted lower alkoxy group, or pyridyl group substituted with at least one substituent selected from the group consisting of lower alkyl group, halogen substituted lower alkyl group, lower alkoxy group and halogen substituted lower alkoxy group, $X^2$ and $X^7$ are the same or different and are halogen atoms, and $X^6$ is a leaving group, the method comprising the steps of:

(a) reacting a compound represented by formula (20) with a compound represented by formula (7), or with a halogenating agent and a compound represented by formula (21) to obtain a compound represented by formula (22);

(b) reducing the compound represented by formula (22) to obtain a compound represented by formula (23);

(c) converting the hydroxyl group of the compound represented by formula (23) into a leaving group ($X^6$) to obtain a compound represented by formula (24);

(d) reacting the compound represented by formula (24) with a compound represented by formula (25) and then treating the resultant with an acid to obtain a compound represented by formula (26); and (e) reacting the compound represented by formula (26) with a compound represented by formula (27) in the presence of a base to obtain the compound represented by formula (2).

* * * * *